(12) United States Patent
Burbank et al.

(10) Patent No.: US 6,602,251 B2
(45) Date of Patent: Aug. 5, 2003

(54) DEVICE AND METHODS FOR OCCLUSION OF THE UTERINE ARTIERIES

(75) Inventors: Fred Burbank, San Juan Capistrano, CA (US); Michael Jones, Capistrano Beach, CA (US); Paul Lubock, Laguna Niguel, CA (US)

(73) Assignee: Vascular Control Systems, Inc., San Juan Capistrano, CA (US)

( * ) Notice: Subject to any disclaimer, the term of this patent is extended or adjusted under 35 U.S.C. 154(b) by 101 days.

(21) Appl. No.: 09/835,402

(22) Filed: Apr. 17, 2001

(65) Prior Publication Data

US 2001/0014805 A1 Aug. 16, 2001

Related U.S. Application Data

(62) Division of application No. 09/207,572, filed on Dec. 8, 1998, now Pat. No. 6,254,601.

(51) Int. Cl.[7] ................................................ A61B 18/18
(52) U.S. Cl. ........................... 606/45; 606/41; 606/46; 128/898; 600/461
(58) Field of Search .......................... 606/41–50, 194, 606/200; 128/830–831, 898; 600/376, 461

(56) References Cited

U.S. PATENT DOCUMENTS

| 4,292,960 A | 10/1981 | Paglione |
| 4,428,379 A | 1/1984 | Robbins et al. |

(List continued on next page.)

FOREIGN PATENT DOCUMENTS

| DE | 195 25 440 A | 2/1997 |
| EP | 0 472 368 | 2/1992 |
| EP | 0 598 579 | 5/1994 |
| EP | 1 072 282 | 1/2001 |
| GB | 2 311 468 A | 1/1997 |
| WO | WO 95/02370 | 1/1995 |
| WO | WO 95/02371 | 1/1995 |
| WO | WO 96/10365 | 4/1996 |
| WO | WO 97/27897 | 8/1997 |
| WO | WO 98/19713 | 5/1998 |

OTHER PUBLICATIONS

*Arterial Embolisation to Treat Uterine Myomata*, J.H. Ravina et al., Sep. 9, 1995, The Lancet, vol. 346, No. 8976, pp. 671–672.
*Endoscopic Ultrasound–Guided Real Time Biopsy of Peri–Intestinal Tumors*, M. Hunerbein et al., 1998, Surgical Technology International VII, pp. 91–95.
*Sonopsy Ultrasound Guided Breast Biopsy*, NeoVision, advertisement.
*Mick 200–TP Applicator Package*, Mick Radio–Nuclear Instruments, Inc., advertisement.
*Seeding Device—Proscan Urologic Ultrasound Imaging System*, Texnar, advertisement.

(List continued on next page.)

*Primary Examiner*—Linda C. M. Dvorak
*Assistant Examiner*—David M. Ruddy
(74) *Attorney, Agent, or Firm*—Coudert Brothers LLP

(57) ABSTRACT

Devices and methods are disclosed for treating a uterine disorder which receive its blood supply from a uterine artery. In particular, uterine fibroids are effectively treated by occluding the uterine arteries using trans-vaginal, trans-uterine, transrectal, or retroperitoneal approaches. The devices and methods are advantageous because the inventive procedures may be performed by a patient's gynecologist in the course of treatment, avoiding the need for referrals to specialist practitioners and for more radical treatments, such as hysterectomies. The methods include both temporary and permanent occlusion of the arteries. A cannula carries an imaging device and a member which will easily penetrate tissue, the member including a device which partially or completely, and temporarily or permanently, occludes a uterine artery.

19 Claims, 25 Drawing Sheets

U.S. PATENT DOCUMENTS

| | | |
|---|---|---|
| 4,509,528 A | 4/1985 | Sahota |
| 4,650,466 A | 3/1987 | Luther |
| 4,757,823 A | 7/1988 | Hofmeister et al. |
| 4,994,069 A | 2/1991 | Ritchart et al. |
| 5,081,997 A | 1/1992 | Bosley, Jr. et al. |
| 5,108,408 A | 4/1992 | Lally |
| 5,201,314 A | 4/1993 | Bosley, Jr. et al. |
| 5,226,911 A | 7/1993 | Chee et al. |
| 5,275,166 A | 1/1994 | Vaitekunas et al. |
| 5,289,831 A | 3/1994 | Bosley |
| 5,336,231 A | 8/1994 | Adair |
| 5,383,922 A | 1/1995 | Zipes et al. |
| 5,456,693 A | 10/1995 | Conston et al. |
| 5,458,596 A | 10/1995 | Lax et al. |
| 5,488,958 A | 2/1996 | Topel et al. |
| 5,507,744 A | 4/1996 | Tay et al. |
| 5,542,944 A | 8/1996 | Bhatta |
| 5,549,624 A | 8/1996 | Mirigian et al. |
| 5,549,824 A | 8/1996 | Trumpf et al. |
| 5,556,396 A | 9/1996 | Cohen et al. |
| 5,588,960 A | 12/1996 | Edwards et al. |
| 5,614,204 A | 3/1997 | Cochrum |
| 5,662,680 A | 9/1997 | Desai |
| 5,672,153 A | 9/1997 | Lax et al. |
| 5,691,314 A | 11/1997 | Hodgen |
| 5,697,942 A | 12/1997 | Palti |
| 5,713,896 A | 2/1998 | Nardelia |
| 5,713,942 A | 2/1998 | Stern et al. |
| 5,715,832 A | 2/1998 | Koblish et al. |
| 5,716,389 A | 2/1998 | Walinsky et al. |
| 5,720,743 A | 2/1998 | Bischof et al. |
| 5,759,154 A | 6/1998 | Hoyns |
| 5,766,135 A | 6/1998 | Terwilliger |
| 5,776,129 A | 7/1998 | Mersch |
| 5,797,397 A | 8/1998 | Rosenberg |
| 5,800,378 A | 9/1998 | Edwards et al. |
| 5,817,022 A | 10/1998 | Vesely |
| 5,836,906 A | 11/1998 | Edwards |
| 5,840,033 A | 11/1998 | Takeuchi |
| 5,895,386 A | 4/1999 | Odell et al. |
| 5,899,861 A | 5/1999 | Friemel et al. |
| 5,910,484 A | 6/1999 | Haupert, Jr. |
| 5,911,691 A | 6/1999 | Mochizuki et al. |
| 5,921,933 A | 7/1999 | Sarkis et al. |
| 5,941,889 A | 8/1999 | Cermak |
| 5,979,453 A | 11/1999 | Savage et al. |
| 6,015,541 A | 1/2000 | Greff et al. |
| 6,019,724 A | 2/2000 | Gronningsaeter et al. |
| 6,032,673 A | 3/2000 | Savage et al. |
| 6,033,398 A | 3/2000 | Farley et al. |
| 6,034,477 A | 3/2000 | Peeters et al. |
| 6,035,238 A | 3/2000 | Ingle et al. |
| 6,045,508 A | 4/2000 | Hossack et al. |
| 6,066,139 A | 5/2000 | Ryan et al. |
| 6,077,257 A | 6/2000 | Edwards et al. |
| 6,106,473 A | 8/2000 | Violante et al. |
| 6,231,515 B1 | 5/2001 | Moore et al. |
| 6,254,601 B1 | 7/2001 | Burbank et al. |
| 6,280,441 B1 | 8/2001 | Ryan |
| 6,425,867 B1 * | 7/2002 | Vaezy et al. ............... 600/439 |

OTHER PUBLICATIONS

*Transrectal Biopsy of the Prostrate Gland*, Bruel & Kjaer Medical Systems, Inc., advertisement.

*Multiplanar Biopsy Transverse Scan*, Bruel & Kjaer Medical Systems, Inc., advertisement.

Burbank, Fred, et al.,*Uterine Artery Occlusion by Embolization or Surgery for the Treatment of Fibroids: A Unifying Hypothesis—Transient Uterine Ischemia*, The Journal of the American Association of Gynecologic Laparoscopists, Nov. 2000, vol. 7, No. 4 Supplement, pp. S3–S49.

Barth, Klemens H. et al., "Long Term Follow–Up of Transcatheter Embolization With Autologous Clot, Oxycel and Gelfoam in Domestic Swine", *Investigative Radiology*, May–Jun. 1977, vol. 12, pp. 273–290.

Bateman, William M.D., "Treatment of intractable menorrhagia by bilateral uterine vessel, Interruption",*Am. J. Obst. & Gynec.*89(6):825–827 (Jul. 15, 1964).

Brigato, G. et al., "A Noninvasive Instrumental Method in Severe Postpartum Hemorrhages", *Minerva Genecologica*50(7–8):337–339(1998).

Brohim, Robert M. et al., "Development of Independent Vessel Security After Ligation With Absorbable Sutures or Clips", *The American Journal of Surgery*, Mar. 1993, vol. 165, pp. 345–348.

Fuchs, Karl, "Afibrinogenemia Treated by Ligation of Uterine Arteries", *Gynacologic*148:407–411 (1959).

Garza Leal, J. et al., "Myoma Treatment by Transient Uterine Ischemia", *The Journal of the American Association of Gynecologic Laparoscopists*7(3):S31 (Aug. 2000).

Hay, D.L. et al., "Hemostasis in Blood Vessels After Ligation", *Am. J. Obstet. Gynecol.*, Mar. 1989, 160:3, pp. 737–739.

O'Leary, James A., M.D., "Uterine Artery Ligation in the Control of Postcesarean Hemorrhage", *The Journal of Reproductive Medicine, Inc.*, 403(3):189–193 (Mar. 1995).

O'Leary, James L., M.D. et al., "Uterine artery ligation in the control of intractable postpartum hemorrhage", Am. J. Obst. & Gynec. 94(7):920–924 (Apr. 1, 1966).

Schaefer, C.J. et al., "Absorbable Ligating Clips", *Surg. Gynecol. Obstet.*, 1982, 154:513–516.

International Search Report for EP 99 96 7154 (PCT/US99/28101) mailed Dec. 3, 2002.

* cited by examiner

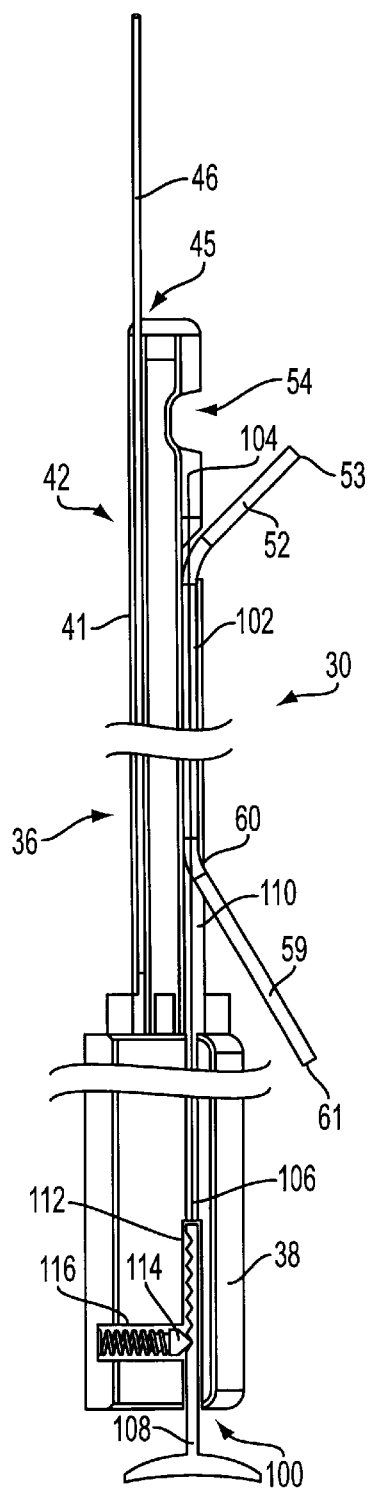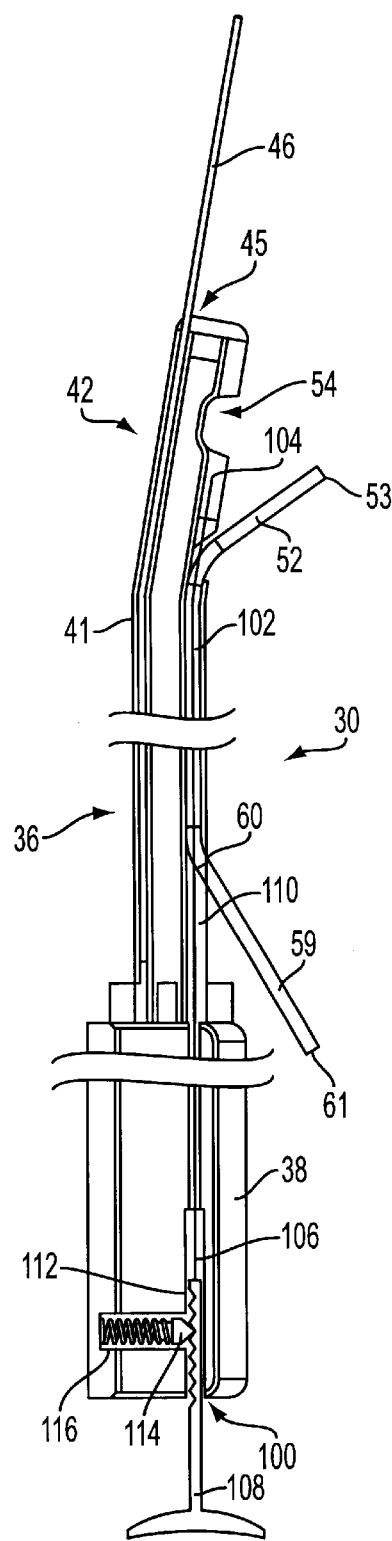
FIG. 6
FIG. 7

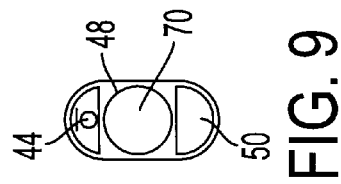
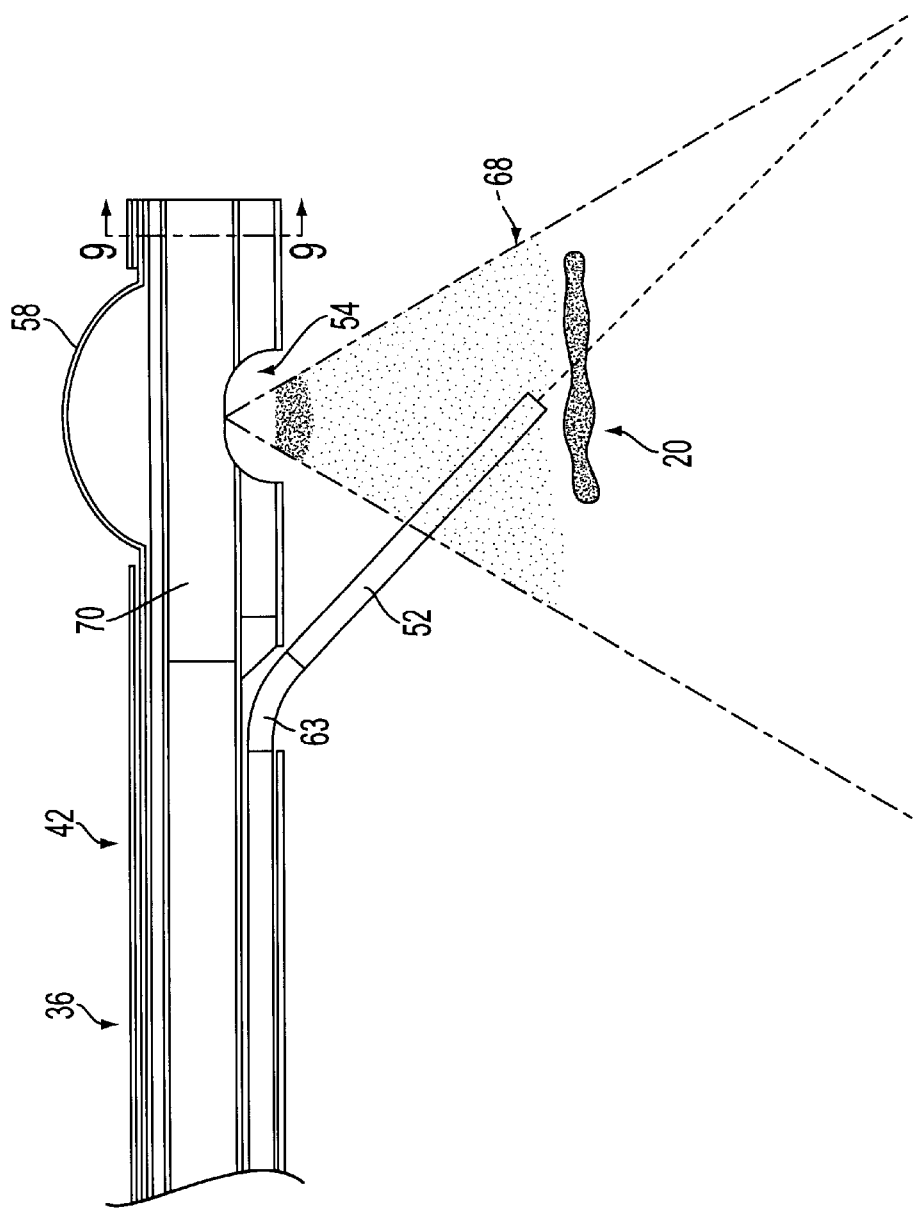

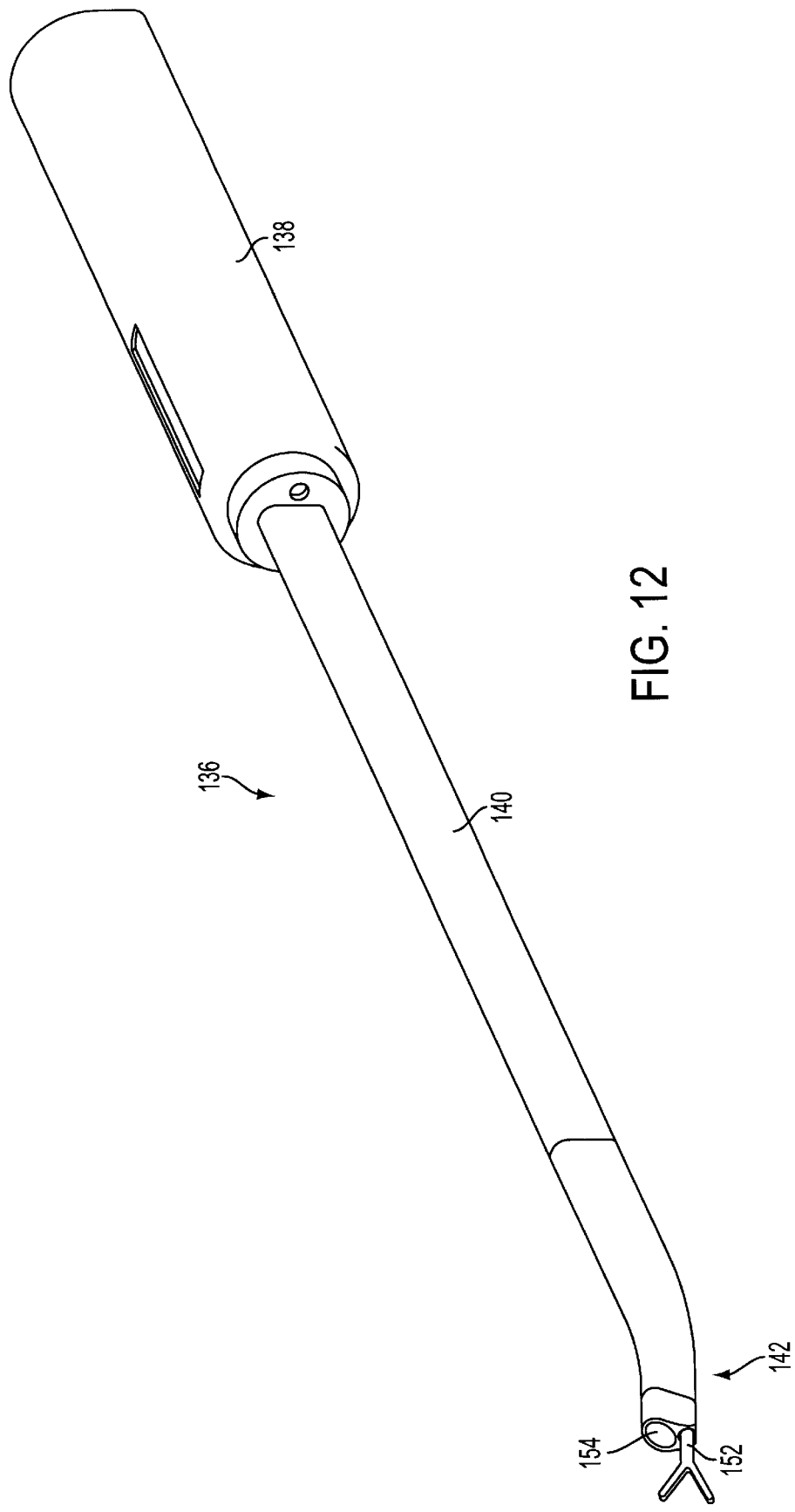

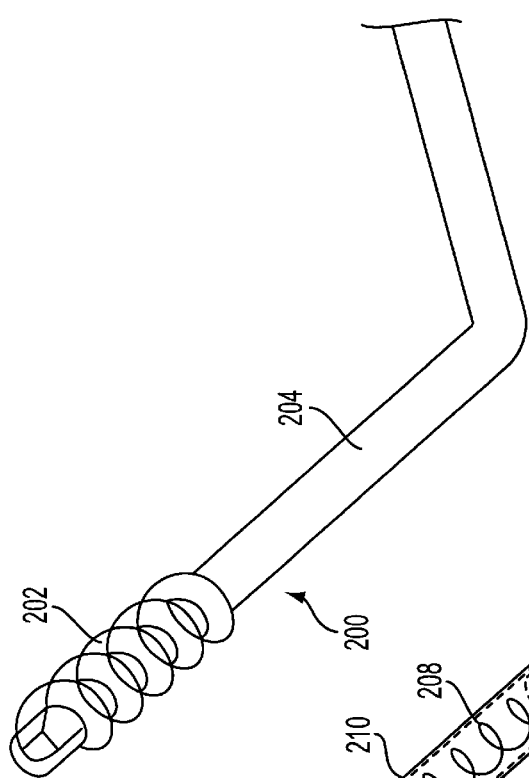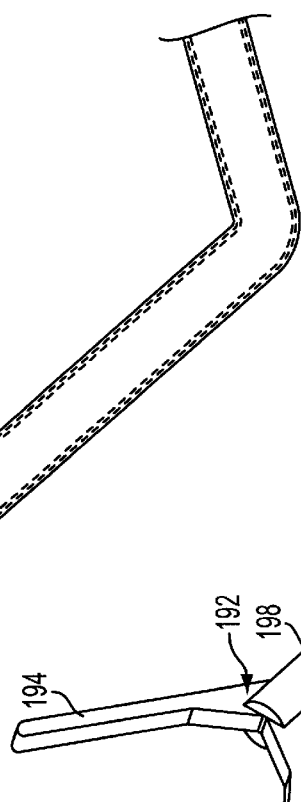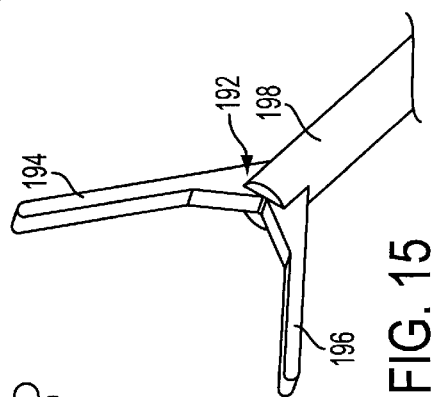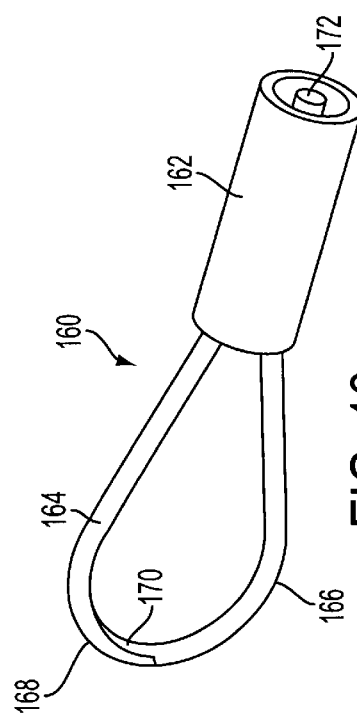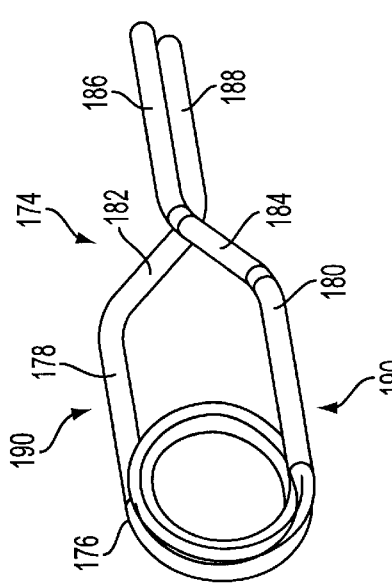

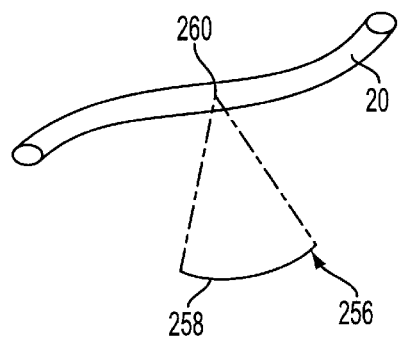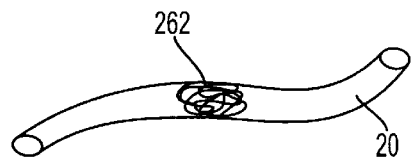
FIG. 29  FIG. 30
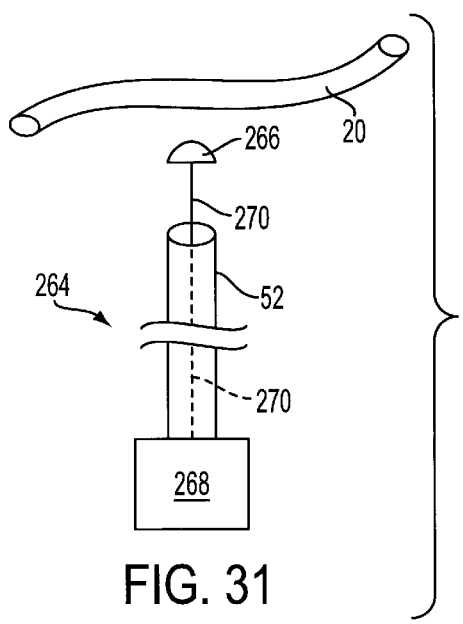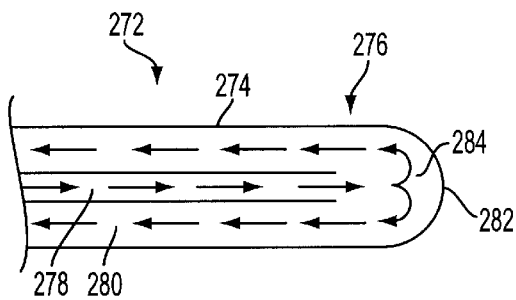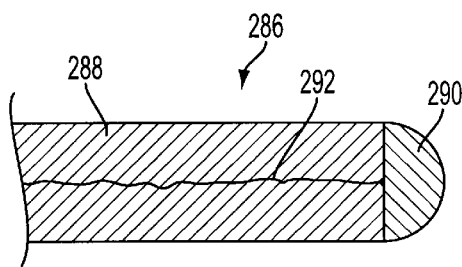
FIG. 31  FIG. 32
FIG. 33

DEVICE AND METHODS FOR OCCLUSION OF THE UTERINE ARTIERIES

This application is a divisional of application Ser. No. 09/207,572, filed on Dec. 8, 1998 now U.S. Pat. No. 6,254,601.

BACKGROUND OF THE INVENTION

1. Field of the Invention

The present invention relates generally to the treatment of disorders which receive blood flow from the uterine arteries, and more particularly to devices and methods for occlusion of the uterine arteries.

2. Brief Description of the Related Art

Hysterectomy (surgical removal of the uterus) is performed on approximately 600,000 women annually in the United States. For approximately 340,000 women, hysterectomy is probably the best current therapeutic choice for the treatment of their diseases (uterine cancer, endometriosis, menorrhagia, and prolapse). For approximately 60,000 women with dysfunctional uterine bleeding (abnormal menstrual bleeding that has no discrete anatomic explanation such as a tumor or growth), newer endometrial ablation techniques may be an alternative to hysterectomy. For approximately 200,000 women with benign but symptomatic (excessive bleeding, pain, and "bulk" sensations) muscular tumors of the uterus, known as leiomyoma or fibroids, newer treatment methods have been developed which may spare these women a hysterectomy, as well.

Hysterectomy for treating uterine fibroid disorders, though effective, has many undesirable characteristics. Thus, any method which can approximate the therapeutic result of a hysterectomy without removing the uterus (and commonly the ovaries since they are closely adjacent to the uterus) would be a significant improvement in this field.

The undesirable characteristics of hysterectomy include a known mortality rate of 0.5 deaths per 1000 hysterectomies. Stated another way, the risk of death within 30 days of hysterectomy is thirty times greater for women who have had a hysterectomy than for women of similar ages and backgrounds who have not had a hysterectomy. Morbidity (medical symptoms and problems short of death) associated with hysterectomy include possible injury to adjacent organs (the bladder, the ureters, and bowel), hospital stay of approximately one week, five to six weeks of slow recovery to normal activity, three weeks of absence from work, direct medical expenses of at least $10,000, indirect cost of time away from work, a future three-fold increase in the incidence of cardiovascular disease, decreased sexual pleasure in approximately thirty percent of women, and depression and anxiety for many years after the hysterectomy for approximately eight percent of women.

The endometrium is a glandular mucous membrane of the uterus, the thickness and structure of which varies with the phase of the menstrual lining. It is normal for portions of the lining to slough off and bleed during menstruation, but many women suffer from painful dysfunctional uterine bleeding or endometritis. Thus, endometrial ablation (removal or destruction of the endometrium) may be an alternative to hysterectomy for approximately 60,000 women. A great many new devices have been invented to perform endometrial ablation to treat dysfunctional uterine bleeding. To distinguish the present invention and its applications from endometrial ablation devices, the endometrial ablation devices will be briefly described. Endometrial devices can be categorized into two major groups: devices which require direct visualization of the endometrium to apply an energy source to ablate the endometrium; and those that do not require visualization for their application.

Direct visualization of the lining of the uterus is accomplished by placing a hysteroscope through the vagina and into the uterus via the cervical os (opening). The hysteroscope image is then displayed as a color image on a TV monitor adjacent to the patient. The gynecologist then manipulates the hysteroscope and endometrial ablation instrument to ablate the lining of the uterus. Endometrial lining ablation instruments directed by hysteroscope include radiofrequency or electrosurgery loops, roller-balls, and lasers. The goal of all of these hysteroscopic endometrial ablation instruments is to transfer heat energy to the endometrium sufficiently to heat and thereby destroy it. An ablated endometrium cannot respond physiologically or pathologically to hormonal stimulation and cannot, therefore, proliferate and bleed.

To treat all of the endometrium, it must be entirely visible through the hysteroscope. However, visualization of all of the endometrium is difficult. The uterus must be distended like a water balloon to allow adequate visualization. In this distension process, some women become water intoxicated and hyponatremic. Furthermore, the uterine cavity is an awkward shape, somewhat triangular and often angulated. Directly visualizing each and every square millimeter of endometrial surface and ablating each and every square millimeter is seldom achieved. Consequently, portions of the dysfunctional endometrium may persist and dysfunctional bleeding may continue.

Because of these hysteroscopic visualization and ablation limitations, alternative methods have been invented to destroy the lining of the uterus without the need at all for visualization of the uterine lining. On such method uses a prototypic instrument, the ThermaChoice™ balloon, which is produced by GyneCare, a division of Ethicon, Inc. (see U.S. Pat. No. 5,776,129, incorporated in its entirety herein). This device is inserted through the vagina into the uterus via the cervical os. The balloon is shaped like a triangle to conform to the shape of the uterus. Once in place, hot fluid is added to the balloon to heat and destroy the uterine lining. Treatment only occurs where the balloon is in adequate contact with the uterine lining. As an alternative, hot fluids can be directly introduced into the uterus (e.g., ENABL brand system manufactured by Innerdyne, Inc., and marketed by U.S. Surgical Corporation).

Endometrial destruction can also be brought about with chemical damage, photochemical injury, or thermal damage (heat or cold). Energy that reaches and destroys the cells of the endometrial lining of the uterus potentially destroys the uterine lining and thereby treats dysfunctional uterine bleeding.

Surgically removing fibroids or in situ ablation of uterine fibroids is a bit like eradicating ants in the pantry—they are not all seen from one perspective and there may be a lot of them. Commonly, a diagnosis of uterine fibroids involves the presence of multiple fibroids, often averaging ten fibroids or more per afflicted uterus. Consequently, it is difficult to know which fibroid is causing symptoms to the patient (bleeding, pain, and bulk effects on adjacent organs). Furthermore, fibroids occur at different layers in the uterus. Uterine fibroids can occur adjacent to the lining of the uterus (submucosal fibroid), in the myometrium (intramural fibroid), or adjacent to the outer layer of the uterus (subserosal fibroid). Consequently, if one is directly observing the uterus from the peritoneal cavity, only subserosal fibroids would be seen. If one is directly observing the uterus from the endometrial surface of the uterus, only the submucosal would be seen. Fibroids deep within the wall of the uterus are poorly visualized from either surface. Finally, since fibroids come in all sizes, only the larger fibroids will be seen in any case.

Clearly, the strategy of identifying which individual fibroid is causing symptoms (when there are often many), finding that fibroid, and then either removing or destroying that individual fibroid is a rather complex strategy. It is therefore easy to understand why the hysterectomy is such a common surgical choice. With hysterectomy, all uterine fibroids are removed in one stroke.

In 1995, it was demonstrated that fibroids, in a uterus that contained one or multiple fibroids, could be treated without hysterectomy using a non-surgical therapy, specifically comprising bilateral intraluminal occlusion of the uterine arteries (Ravina et al., "Arterial Embolization to Treat Uterine Myomata", *Lancet* Sep. 9, 1995; Vol. 346; pp. 671–672, incorporated in its entirety herein). This technique is known as "uterine artery embolization". The technique uses standard interventional radiology angiographic techniques and equipment, whereby the uterine arteries are accessed via a transvascular route from a common femoral artery into the left and right uterine arteries.

Three facts explain the success of uterine artery embolization. First, it has been established that pelvic bleeding from a wide variety of sources (e.g., auto accidents, surgical errors, and post partum hemorrhage) can be effectively controlled with embolization techniques using coils placed in arterial and venous lumens (U.S. Pat. Nos. 4,994,069, 5,226,911, and 5,549,824, all of which are incorporated in their entireties herein) (available from Target Therapeutics), or particles (GELFOAM pledgets, available from Upjohn, Kalamazoo, Michigan, or IVALON particles, available from Boston Scientific).

Second, fibroids live a tenuous vascular life with very little ability to recruit a new blood supply from the host when the primary blood supply is compromised. Third, the uterus has a dual (or redundant) blood supply; the primary blood supply is from the bilateral uterine arteries, the secondary blood supply from the bilateral ovarian arteries (see FIG. 4).

Consequently, when both uterine arteries are occluded, i.e. bilateral vessel occlusion, the uterus and the fibroids contained within the uterus are both deprived of their blood supply. However, as demonstrated by Ravina et al., the effect on the fibroid is greater than the effect on the uterus. In most instances, the fibroid withers and ceases to cause clinical symptoms.

The uterine artery embolization technique utilized by Ravina et al. uses standard transvascular equipment, available in typical interventional radiology angiography suite. This equipment includes guide catheters to selectively enter the tortuous right and left uterine arteries, Ivalon or Gelfoam particles, and intravascular coils. With skill and these standard angiographic tools, the uterine arteries can be occluded bilaterally and fibroid disease treated through a 2 mm hole in the right groin and through the right common femoral artery. Following the procedure, the arterial puncture site is held with manual pressure for fifteen minutes. While post-procedural pain is often significant, and requires intravenously delivered pain medication, the patient is typically fully recovered in a few days.

The problem with uterine artery embolization is simple. The physicians who know how to do the procedure are interventional radiologists, who do not take care of gynecology problems. The physicians who take care of gynecology problems do not possess the skill necessary to perform catheter based uterine artery embolization. Accordingly, only hundreds of uterine artery embolizations have been performed, worldwide, over the past three years, whereas hundreds of thousands of hysterectomies have been performed each year for uterine fibroids which are symptomatic.

What is needed, therefore, are devices and methods which allow an average gynecologist to occlude the uterine arteries through a transvaginal approach, the standard site of access for evaluating and treating gynecologic disease.

SUMMARY OF THE INVENTION

In accordance with a first exemplary embodiment of the present invention, a system for treating disorders which receive blood from the uterine arteries by causing at least partial occlusion of a uterine artery comprises means for sensing a location of a uterine artery; and means for at least partially penetrating an anatomical structure in the region of the uterine artery to cause at least partial occlusion of the uterine artery to thereby decrease the blood flow to the uterus and said disorder.

In accordance with a second exemplary embodiment of the present invention, a system for treating disorders in a human female, which receive blood from at least one of the uterine arteries, by causing at least partial occlusion of a uterine artery comprises a cannula having a proximal end and a distal end, an ultrasonic transducer positioned adjacent said distal end, said ultrasonic transducer capable of sensing the location of anatomical structures in a sensing plane when energized, and a tissue penetrating member having a distal end and being movable relative to said cannula between a retracted position and a extended position, said tissue penetrating member distal end being substantially in said sensing plane when said tissue penetrating member is in said extended position.

In accordance with a third exemplary embodiment of the present invention, a system for treating disorders in a human female, which receive blood from at least one of the uterine arteries, by effecting at least partial occlusion of a uterine artery comprises a locating cannula having a proximal end and a distal end, said locating cannula including a locating device positioned adjacent said distal end, said locating device capable of sensing the location of anatomical structures in at least a sensing plane when energized, and a tissue penetrating cannula having a distal end and including a tissue penetrating member, said tissue penetrating cannula being movable independent from and relative to said locating cannula between a retracted position and a extended position, said tissue penetrating member distal end being substantially in said sensing plane when said tissue penetrating member is in said extended position.

In accordance with a fourth exemplary embodiment of the present invention, a method of treating a disorder that receives blood from at least one uterine artery by at least partially cutting off the blood supply to said disorder comprises the steps of penetrating tissue to reach a point adjacent said uterine artery, and occluding said uterine artery to at least partially cut of the blood supply to said disorder.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to preferred embodiments of the apparatus and method, given only by way of example, and with reference to the accompanying drawings, in which:

FIGS. 6 and 7 are perspective illustrations of a second exemplary embodiment of an apparatus in accordance with the present invention;

FIG. 8 is a schematic illustration of a distal end portion of an apparatus in accordance with the present invention, and illustrating an imaging plane;

FIG. 9 is a cross-sectional view of the embodiment illustrated in FIG. 8, taken at line 9—9;

FIG. 12 is a schematic illustration of an endviewing embodiment of an apparatus in accordance with the present invention;

FIGS. 13–33 schematically illustrate several additional exemplary embodiments of apparatus in accordance with the present invention;

DESCRIPTION OF THE PREFERRED EMBODIMENTS

Figure 2:
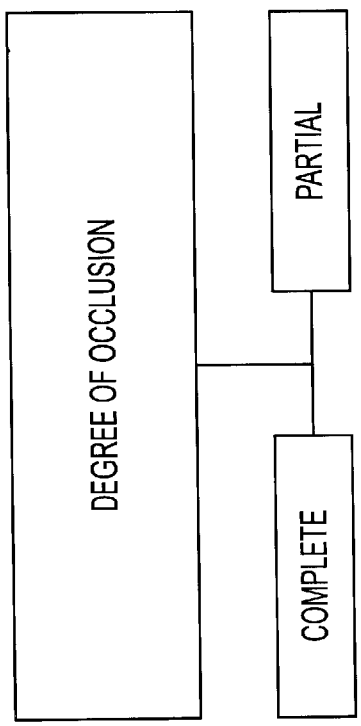
FIG. 2 is an illustration of a second treatment option in accordance with the present invention.

Neither image-directed endometrial ablation nor non-image-directed endometrial ablation is presently utilized to treat uterine fibroids, the subject of the present application. In fact, the presence of uterine fibroids may be a contraindication for the use of any of the endometrial ablation techniques, since the fibroid might be eroded by the endometrial ablation and thereby be stimulated to bleed uncontrollably.

The present invention is directed to the problem of treating the 200,000 women who annually undergo hysterectomy for symptomatic fibroid disease. Therapies have been devised to also treat uterine fibroids without hysterectomy. For example, surgical methods (both open, interventional surgery and endoscopic/hysteroscopic surgery) have been developed to destroy fibroids (myomas) in situ (myolysis). Myomectomy uses standard or miniature surgical instruments to cut a fibroid away from the uterus. After the fibroid is cut away, the uterine muscle is then sutured back together. Myolysis is a process by which probes are used to focus energy directly into the fibroid to heat the fibroid tissue sufficiently to destroy the fibroid. Energy sources such as laser, radiofrequency energy, and microwave energy have been used for this purpose.

The present invention solves the problems outlined above by providing devices and methods for treating uterine disorders, particularly uterine fibroids, by occluding the uterine arteries using trans-vaginal, trans-uterine, trans-rectal, and retroperitoneal approaches. An important advantage of the invention is that the inventive procedures may be performed by a patient's gynecologist in the course of treatment, avoiding the need for referrals to specialist practitioners and for more radical treatments, such as hysterectomies.

Referring to the drawing figures, like reference numerals designate identical or corresponding elements throughout the several figures.

Figure 1:
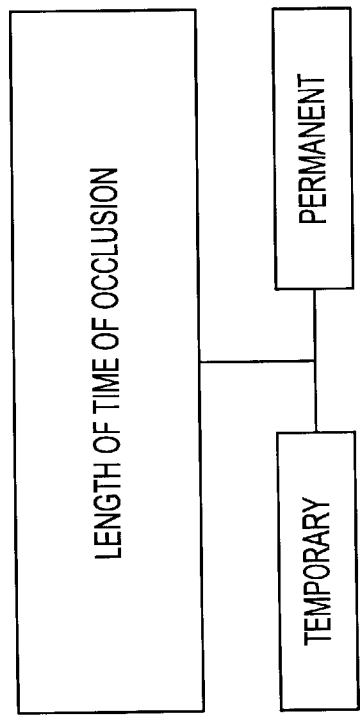
FIG. 1 is an illustration of a treatment option in accordance with the present invention.

FIGS. 1 and 2 illustrate two different treatment options or variables the values of which can be achieved with systems and processes in accordance with the present invention. FIG. 1 illustrates that the present invention is usable for both temporary and permanent occlusion of the uterine artery or arteries, while FIG. 2 illustrates that the present invention is usable for either complete or partial occlusion. The four permutations available through these different modalities enable the practitioner to customize treatment for a particular patient based upon the doctor's evaluation of the patient's clinical symptoms, as well as other factors which bear on the decision to treat uterine myomas with the system and processes of the present invention.

Figure 3:
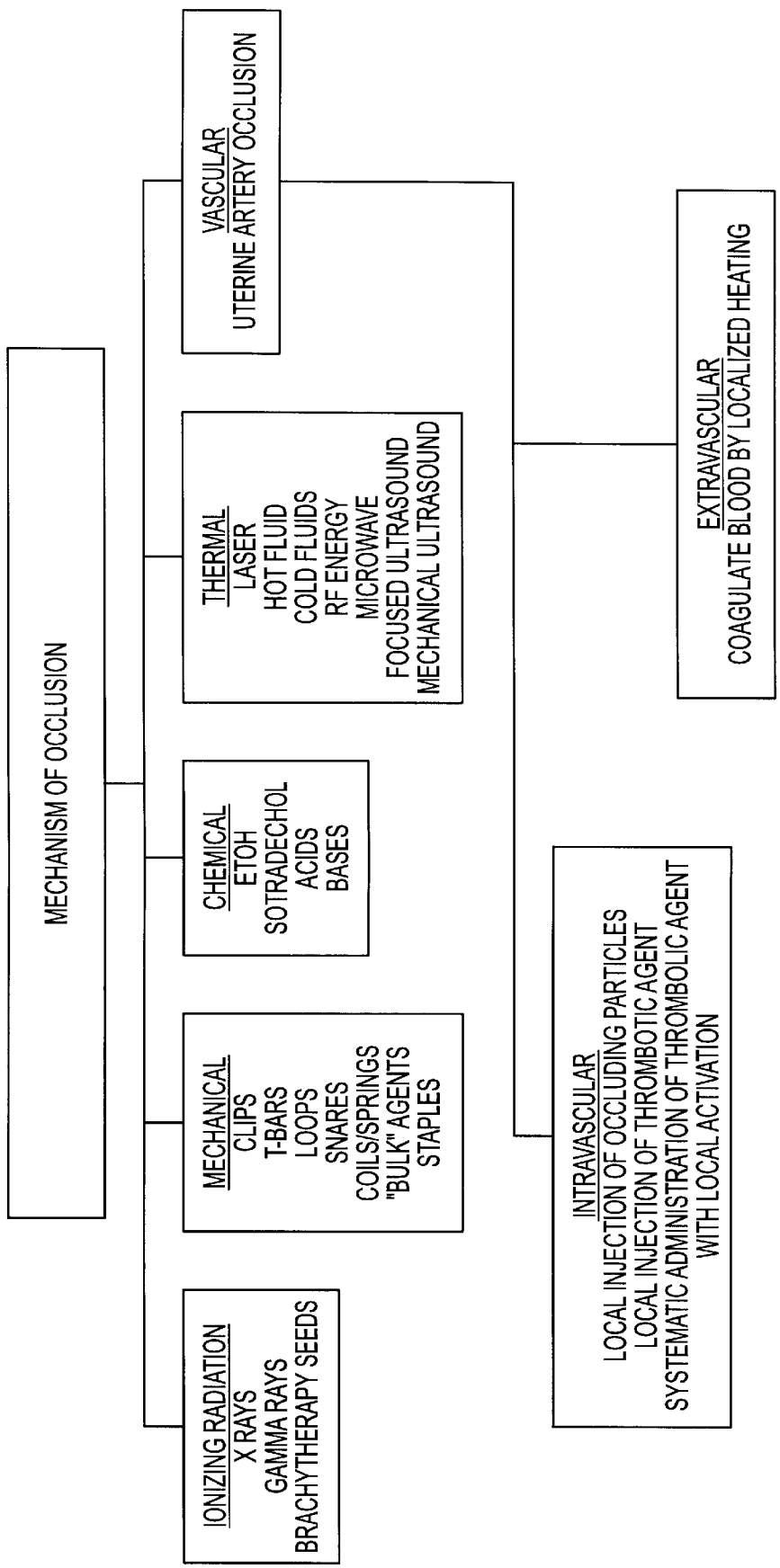
FIG. 3 is an illustration of relationships between several mechanisms of occlusion of uterine arteries in accordance with the present invention.

FIG. 3 illustrates relationships between the mechanisms of occluding the uterine arteries which form a part of the system and processes of the present invention. There are at least five general mechanisms which can be used, either individually or in combinations, to occlude the uterine arteries. Ionizing radiation, which includes X rays, gamma rays, and radiation from brachytherapy seeds (radioactive particles), can be focused on the uterine arteries and surrounding tissues at high energy levels to kill this tissue, which initiates a clotting sequence in the uterine artery leading to total occlusion. Mechanical occlusion, including occlusion using clips, T-bars, loops, snares, coils or springs, "bulk" agents, and staples, involves capturing and crushing the uterine artery (and likely adjacent tissue) to mechanically reduce or cut off the flow of blood therethrough.

Chemical occlusion of the uterine arteries in accordance with the present invention includes injecting or otherwise exposing the uterine artery and adjacent tissue, if convenient or necessary, to chemical agents which cause tissue necrosis, which also initiates a clotting sequence. Such chemical agents include ethyl alcohol (EtOH), Sotradechol, and generally strong acids and bases which can be locally administered without causing systemic toxicity. Thermal occlusion can include lasers, hot fluids, cold fluids, radio frequency (RF) energy, microwave energy, focused ultrasound, and mechanical ultrasound, by which the uterine arteries are heated to temperatures which cause cell death, typically above 45° C., preferably between about 60° C. and about 70° C., which also initiates a cascade which causes vessel occlusion.

Vascular uterine artery occlusion involves at least intravascular and extravascular modalities. Intravascular initiation of an embolism that will cause uterine occlusion, in accordance with the present invention, includes injection of occluding particles and/or thrombotic agents directly into the uterine arteries so that a clotting sequence is rapidly commenced, terminating in uterine artery occlusion. In a similar manner, an agent which can initiate a clotting sequence can be administered systemically, yet only activated in the uterine artery (e.g, by EM radiation, heat transfer, or chemical interaction) by localizing and focusing an activation energy or compound only in the uterine arteries. Extravascular initiation of embolism in the uterine arteries can be accomplished by, e.g, heating the blood extravascularly in the uterine arteries to coagulate the blood, thereby initiating a clotting sequence.

As will be readily appreciated by one of ordinary skill in the art, the modalities described above are merely exemplary, and other equivalent modalities are also within the spirit and scope of the present invention. For example, combining two or more modalities for occlusion of a single uterine artery is also within the scope of the present invention. By specific example, and not by way of limitation, a embolism in and occlusion of a uterine artery can be effected in accordance with the present invention by mechanically closing a uterine artery, and injecting an agent into the artery (and surrounding tissue, if necessary or convenient) which initiates a clotting sequence in the quiescent arterial blood, waiting a proscribed time to allow the blood to fully clot, and removing the mechanical clamping, leaving the uterine artery relatively intact, yet fully occluded. Other combinations of two or more mechanisms of occlusion of the uterine arteries will be readily apparent to one of ordinary skill in the art.

Figure 4:
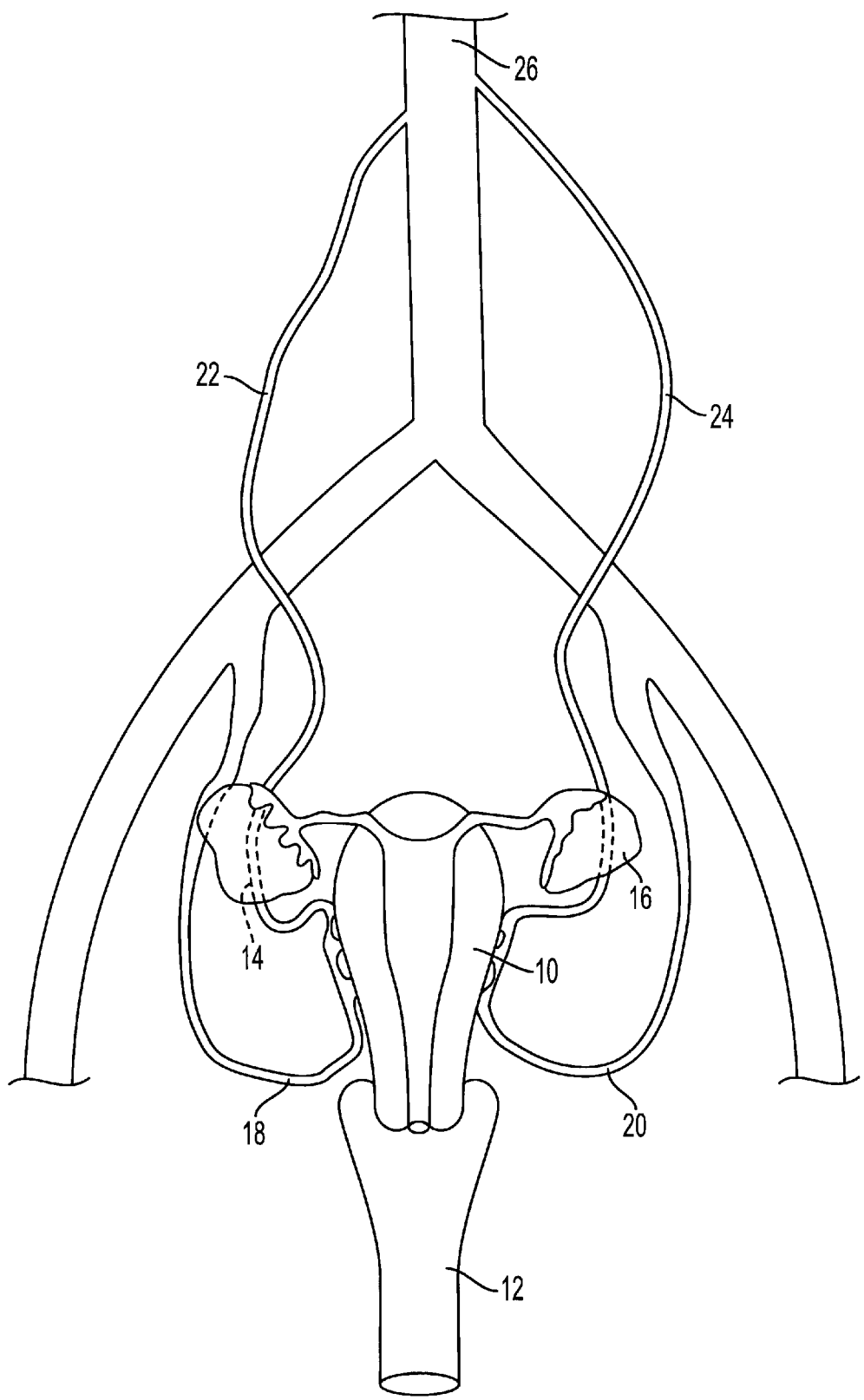
FIG. 4 is a schematic view illustrating the reproductive anatomy of a typical human female patient, including, in particular, the vagina, the uterus, and the left and right uterine arteries.

FIG. 4 illustrates a typical reproductive system for a human female patient, including a uterus 10, vagina 12, right ovary 14, and left ovary 16. Blood is supplied to the uterus 10 primarily via the right uterine artery 18 and the left uterine artery 20, and secondarily via the right ovarian artery 22 and the left ovarian artery 24, all of which are supplied by the aorta 26.

Figure 5:
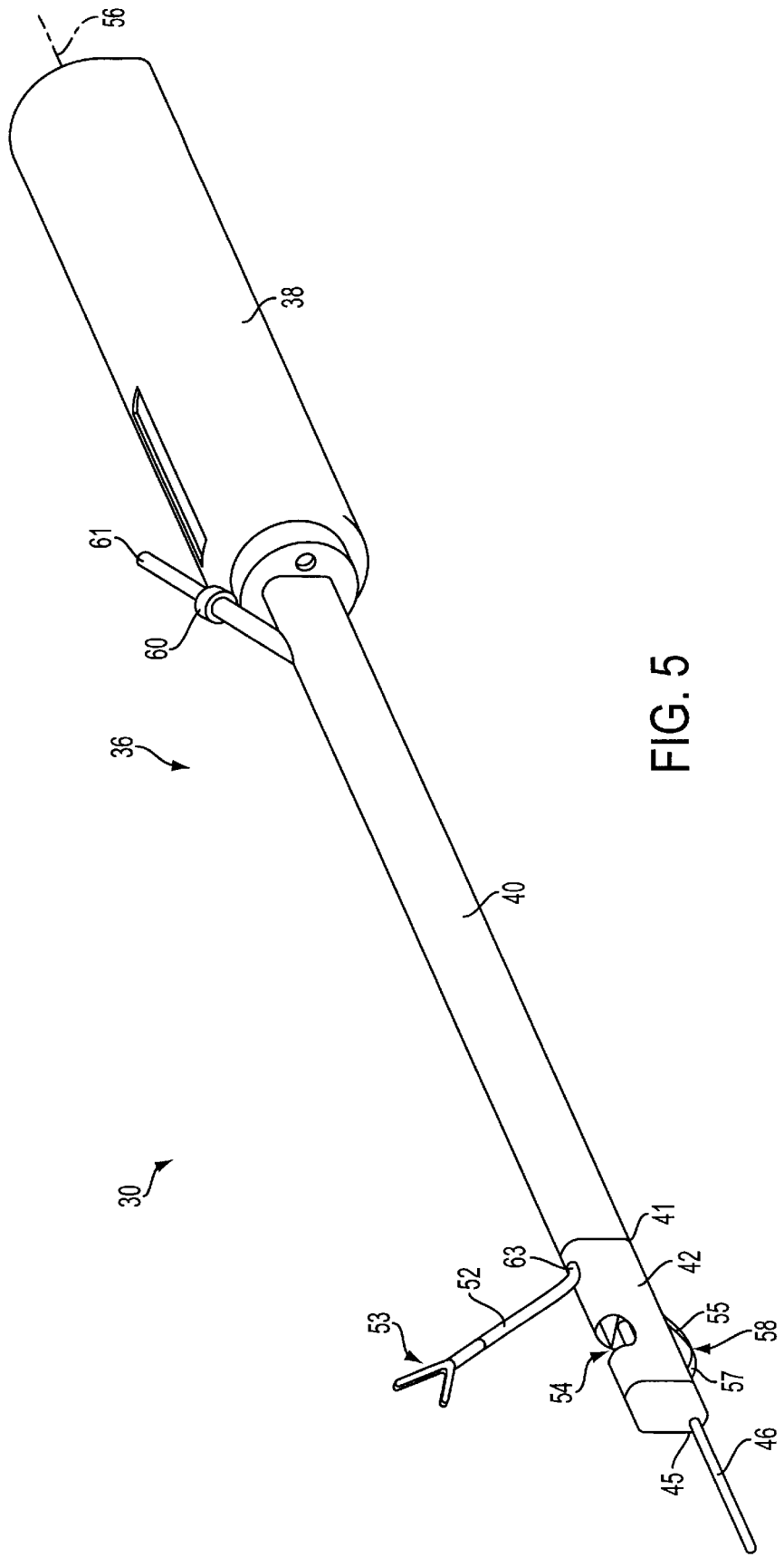
FIG. 5 is a perspective illustration of a first exemplary embodiment of an apparatus in accordance with the present invention.

FIG. 5 illustrates a first exemplary embodiment of an intrauterine instrument 30 in accordance with the present invention constructed to enable a practitioner to readily occlude the uterine arteries. Instrument 30 includes a proximal handle 38 and a cannula 36. Cannula 36 includes a rigid shaft 40 and a distal portion 42. Cannula 36 preferably includes a first lumen 44 (see FIG. 9) which extends from the proximal end of instrument 30 to a distal port 45. A guidewire 46 is positioned in lumen 44 and is movable out distal port 45 and sufficiently rigid to guide cannula 36 into the uterus of a patient, yet flexible enough to conform to the shape of a uterus without damaging it.

A supporting member 58 is positioned in distal portion 42, and extends or is extendable away from cannula 36 to push against a uterine wall, deflect distal portion 42 toward an opposite uterine wall, and support the cannula in the uterine cavity, as described in greater detail below. Distal portion 42 of cannula 36 also includes an imaging window 54 on a side of the cannula opposite supporting member 58, so that when the supporting member bears against a uterine wall, the window is pressed up against an opposite uterine wall.

As illustrated in FIG. 5, supporting member 58 includes a band or belt 55 which is laterally flexible, to allow the belt to be flexed in and out, yet longitudinally rigid, so the supporting member does not collapse. Suitable materials for belt 55 include some stainless steels, nickel/titanium alloys, polymers, composite materials, and other materials which will be readily apparent to one of ordinary skill in the art. The distal end 57 of belt 55 is preferably attached to cannula 36. The proximal end of belt 55 (not illustrated) is preferably longitudinally movable to flex or bow the belt in and out to bear against a uterine wall, causing cannula 36 to move toward the opposite uterine wall. According to an alternate embodiment of the present invention, the proximal end of belt 55 can also be immovably attached to cannula 36, with a middle section which protrudes away from cannula 36 as illustrated in FIG. 5. In this alternate embodiment, belt 55 presses against a uterine wall a predetermined amount when inserted into a uterine cavity.

Cannula 36 is further provided with a tissue, preferably uterine tissue, penetrating member 52, which extends distally through rigid shaft 40 from a proximal port 60 to a distal guide port 63 in distal portion 42. Member 52 is guided by and extendable out of guide port 63 so that a distal end 53 of the tissue penetrating member is substantially in the same plane as an imaging, viewing, or sensing plane of a locating device carried by instrument 30, described in greater detail below. Guide port 63 guides member 52 so that distal end 53 remains in this plane (see FIG. 8), so that procedures which are performed by means of the tissue penetrating member can be viewed by the practitioner without the need for aligning a viewing device and the tissue penetrating member.

Member 52 includes a device on distal end 53 which allows the member to penetrate the muscular uterine wall tissue. In accordance with a first embodiment of the present invention, this penetrating device is a hollow needle including a bore large enough to pass instruments therethrough. In accordance with a second embodiment of the present invention, penetrating device includes an RF energy cutting element and an RF energy conducting wire extending from the cutting element proximally through instrument 30 to an RF generator (not illustrated). RF energy is preferably utilized in the present invention for penetrating the uterine wall, because it cauterizes as it cuts through tissue, resulting in substantially less bleeding. Furthermore, RF energy cutting very efficiently cuts tissue, resulting in relatively effortless advancement of tissue penetrating member 52 into and through the uterine wall toward the uterine artery.

The junction 41 between rigid shaft 40 and distal portion 42 can be either rigid or flexible, and if rigid, either straight or angled. Preferably, junction 41 is flexible so that distal portion 42 can be deflected to one side of longitudinal axis 56 by supporting member 58, as described above. Optionally, instrument 30 can include a pullwire system, described in greater detail below with reference to FIGS. 6 and 7, which operates in conjunction with or in place of supporting member 58 to deflect distal portion 42. Less preferably, yet still within the scope of the present invention, junction 41 can be rigid. Distal portion 42 can be rigidly attached to rigid shaft 40 at a predetermined angle (not illustrated) which would allow the practitioner to insert instrument into a uterine cavity and easily press viewing window 54 against a uterine wall, while supporting member 58 maintains this orientation. Even less preferable, yet still within the scope of the present invention, junction 41 can be rigid and straight.

Turning now to FIGS. 6 and 7, yet another embodiment of instrument 30 is schematically illustrated. In the embodiment illustrated in FIGS. 6 and 7, junction 41 is flexible so that distal portion 42 can be flexed from a straight orientation (FIG. 6) to a flexed orientation (FIG. 7), for the reasons stated above. FIGS. 6 and 7 also illustrate a pullwire system 100 which assists in flexing or bending cannula 36 at junction 41, in addition to or instead of supporting member 58, and holding the cannula in this orientation. Pullwire system 100 includes a longitudinally rigid wire 102 extending from a distal end 104 which is rigidly attached to cannula 36 in distal portion 42, and a proximal end 106 which is attached to a pullwire handle 108. Handle 108 is slidably received in handle 38, and pullwire 102 is slidably received in a lumen 110 which extends parallel to tissue penetrating member 52. Handle 108 includes a set of teeth 112 against which a detent 114 is forced by a spring 116. The combination of spring 116, detent 114, and teeth 112 result in handle 108 being held in discrete, particular longitudinal positions. As will be readily appreciated by one of ordinary skill in the art, pulling proximally on handle 108 results in pullwire 102 deflecting distal portion to the right in FIGS. 6 and 7, which position is maintained without further user action by detent 114 acting on teeth 116.

FIGS. 8 and 9 illustrate cannula 36 being used to visualize, provide an image of, or otherwise sense the position and location of a uterine artery 20. A locating device 70 is mounted in distal portion 42. Locating device 70 can be an ultrasonic imaging device, a gray scale color 2D (Duplex) Doppler ultrasound system, available, for example, from Diasonics, of Santa Clara, Calif., Doppler audio ultrasound systems or other locating systems which are generally available to and used in gynecological practice, including other conventional ultrasound systems as will be readily apparent to one of ordinary skill in the art. Locating device can be a combination of systems, e.g., a 2D (Duplex) Doppler ultrasound system with a Doppler audio ultrasound system, a less complicated, single system, e.g., Doppler audio ultrasound system alone, or even a simple landmarking system, e.g., markings on the outer wall of the cannula so a practitioner can visually determine the location of the cannula relative to anatomical features of the patient. A Doppler audio ultrasound system can advantageously be used by the practitioner listening for an increase in the magnitude of sound produced by the system, which indicates an increase in blood flow velocity near the focal point of the system. Additional details of such Doppler audio ultrasound systems will be readily apparent to one of ordinary skill in the art.

In the embodiment illustrated in FIG. 8, ultrasound imaging device 70 generates an image in a plane or portion of a plane 68, which is pointed or directed through viewing window 54. As discussed above, tissue penetrating member 52 is extendable into and along this plane 68, so that distal tip 53 (not illustrated in FIG. 8 for ease of visualization) of member 52 can be visualized by device 70 while penetrating the uterine wall toward uterine artery 20. The alignment of the sensing or viewing plane of device 70 and tissue penetrating member 52 allows the gynecologist to easily find and occlude the uterine artery with instruments and processes in accordance with the present invention.

FIG. 9 illustrates a cross-sectional view of cannula 36, taken at line 9—9 in FIG. 8. A lumen 44 is illustrated through which guidewire 46 (not illustrated in FIGS. 8 and 9) extends, a lumen 48 in which viewing device 70 is mounted, and a lumen 50 through the proximal portions of which tissue penetration member 52 extends.

Figure 10:
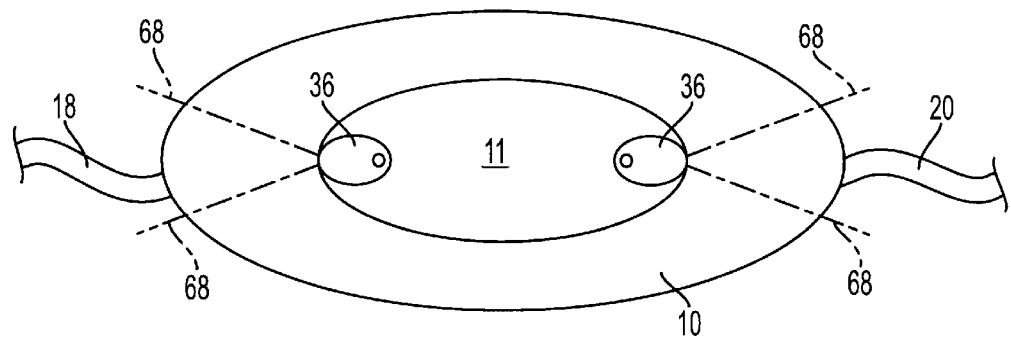
FIG. 10 is an illustration of a cross-section of a uterus in which an apparatus in accordance with the present invention has been located.

FIG. 10 is a schematic illustration of a cross-sectional view of a uterus 10 in which a cannula 36 has been inserted. Uterus 10 includes a uterine cavity 11, and is supplied blood primarily by uterine arteries 18 and 20. Cannula 36 is insertable into uterine cavity 11 (described in greater detail below) and deflectable, either by flexing at junction 41 (see FIGS. 5–7) or by deflection of a rigid cannula, so that the cannula bears against a uterine wall. Cannula 36 can be rotated around axis 56 (not illustrated in FIG. 10; see FIG. 5) so that viewing plane 68 can sweep out a volume in which the uterine arteries lie. Thus, the uterine arteries can be readily located through the uterine wall via a intrauterine approach.

Figure 11:
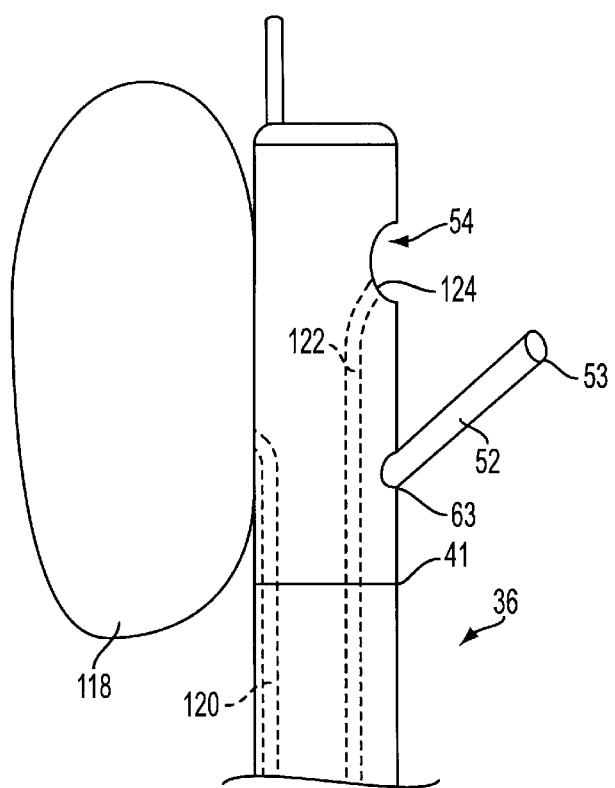
FIG. 11 is a schematic illustration of a yet another exemplary embodiment of an apparatus in accordance with the present invention.

FIG. 11 illustrates yet another exemplary embodiment of an instrument in accordance with the present invention. Similar to the embodiments previously described, cannula 36 has a junction 41, and a tissue penetrating member 52 having a distal end 53 extends out a guide port 63. A viewing window 54 is provided for an imaging device (not illustrated). An inflatable balloon 118 is provided in the place of belt 55, and is inflatable by injecting fluid through a lumen 120 which extends proximally through cannula 36. Inflatable balloon 118 is inflatable to bear against a uterine wall to support cannula 36 against an opposite uterine wall. Cannula 36 further includes a lumen 122 which extends proximally from a distal port 124. Lumen 122 is provided to allow a liquid, gel, or other medium which acts as an acoustic coupler for an ultrasound device mounted within cannula 36, to be injected out or immediately adjacent to viewing window 54. As will be readily appreciated by one of ordinary skill in the art, proper visualization using ultrasound equipment requires that the ultrasound transducer 70 not be separated from the tissue through which it is viewing by any air gap. An air gap between the transducer and the tissue causes reflections, which do not allow the ultrasound waves to travel into the tissue. An acoustic coupling medium, such as a commercially available ultrasound gel, eliminates such air gaps. Thus, lumen 122 is provided to allow a practitioner to inject such an acoustic coupling medium into the viewing window so an ultrasound viewing device 70 can properly produce an image of the uterine tissues.

FIG. 12 illustrates yet another embodiment in accordance with the present invention. A cannula 136 includes a rigid shaft 140 to which a handle 138 is attached. Cannula 136 does not include a flexible portion, but may optionally include a bent distal portion 142. A viewing window 154 is provided at the distal end of cannula 136, directed distally. Similarly, a tissue penetrating member 152 is provided which is extendable distally from the distal end of cannula 136. Similar to the embodiments previously described, tissue penetrating member 152 is extendable into and along the plane of an imaging device (not illustrated in FIG. 12) which is mounted in the distal end of cannula 136, and which directs its viewing plane distally of the cannula distal end.

FIGS. 13–33 illustrate numerous exemplary embodiments of devices for at least partially, and optionally completely occluding a uterine artery. The numerous devices are preferably used as expedients for achieving the four permutations described with reference to FIGS. 1 and 2, and are merely representative of mechanisms of occlusion within the spirit and scope of the present invention. The embodiments illustrated in FIGS. 13–33 preferably share at least one common characteristic: they are each extendable through or with tissue penetrating member 52 or 152 through the uterine or vaginal wall of a patient to the uterine artery of interest. For this purpose, tissue penetrating member 52 or 152 further includes a lumen 59 extending between a proximal end 61 and distal end 53, which allows a practitioner to push one of the devices through the tissue penetrating member 52 or 152 to effect occlusion of a uterine artery.

Turning now to the individual drawing figures, FIG. 13 illustrates a snare 160 which is sized to pass through lumen 59. Snare 160 includes a tubular shaft 162 which is resiliently flexible to allow the snare to be extended through lumen lumen 59, and rigid enough to avoid kinking. Snare 160 includes two interlocking fingers 164, 166 which extend out of shaft 162 and include interlocking portions 168, 170 at their respective distal end. The proximal ends of fingers 164, 166 (not illustrated) are hinged together, and are attached to a longitudinally extending actuating rod 172. Fingers 164, 166 are biased away from each other by their own resilience, so that interlocking portions 168, 170 open to allow snare 160 to be advanced over a uterine artery.

To use snare 160 to occlude a uterine artery, shaft 162 is advanced out the distal end 53, 153 of tissue penetrating member 52, 152 after the member has penetrated the uterine wall and is adjacent the uterine artery of interest. Imaging device 70 allows a practitioner to accurately position distal end 53, 153 adjacent the uterine artery. Rod 172 is then pushed, allowing fingers 164, 166 to separate. The snare is then advanced over the uterine artery and adjacent tissues, and rod 172 is pulled back. Snare 160 is sized so that when interlocking portions 168, 170 meet, snare 160 crushes the uterine artery, and immediately adjacent tissues if necessary or convenient, thus forming an occlusion. These steps are then reversed for removing snare 160, leaving the uterine artery crushed and occluded.

FIG. 14 illustrates a clip 174, similar in structure to a typical aneurysm clip. Clip 174 includes a spring formed of a resilient material, such as a titanium or stainless steel alloy, and having a coiled spring 176. The ends of spring 176 are connected to two actuation portions 178, 180, each actuation portion having an angled extension 182, 184 which angle toward each other. A pair of jaws 186, 188 are provided on the ends of the extensions 182, 184. As will be readily appreciated by one of ordinary skill in the art, jaw 186, 188 are biased toward each other by spring 176. When angled extensions 178, 180 are pressed toward each other by an opening force along vector 190, the jaws open against a spring reaction force generated by the spring; when the opening force along vector 190 is zero, the spring biases the jaws toward each other to close the jaws, illustrated in FIG. 14.

To use clip 174 to occlude a uterine artery, the clip is advanced out of distal end 53, 153 of tissue penetrating member 52, 152 with an actuator (not illustrated) which applies a force along vector 190 to open jaws 186, 188. The open jaws 186,188 are advanced around a uterine artery of interest, and adjacent tissues if convenient. The actuator then releases clip 174, which clamps onto the uterine artery, crushing and occluding it. Clip 174 is left in position on the uterine artery, and the actuator is retracted.

FIG. 15 illustrates a clamp or staple applier 192 which can be used in a fashion similar to snare 160. Clamp 192 includes two jaws 194, 196 which are biased apart and are hinged to an actuating rod 198. The use of clamp 192 to occlude a uterine artery is somewhat similar to the use of snare 160, except that jaws 194, 196 are forced closed by distal end 53,153 of tissue penetrating member 52, 152, in a manner similar to shaft 162. Jaws 194, 196 are advanced out of distal end 53, 153 and around a uterine artery of interest. Tissue penetrating member 52, 152 is then farther distally advanced to bear on the outer portions of jaws 194, 196, forcing the jaws toward each other to crush the uterine artery between them. When used as a staple applier 192, jaws 194, 196 include an anvil (not illustrated) therebetween for a staple to be deformed against.

A discussed briefly above, another example of incorporating multiple mechanisms of occlusion (see FIG. 3) of a uterine artery is to form actuating rod 198 and jaws 194, 196 of a material which allows the jaws to function as a heater to close, seal, or otherwise occlude the uterine artery and adjacent tissue caught between them. By connecting rod 198 to an appropriate electric source, and forming jaws 194, 196 of a resistive heating material, the partially or completely crushed uterine artery can be further occluded by heating the vessel tissues, blood, or both sufficiently to cause an embolism to form in the uterine artery. As will be readily appreciated by one of ordinary skill in the art, combining two or more mechanisms of occlusion in accordance with the principles of the present invention allows a practitioner to more confidently occlude a uterine artery, because the plurality of mechanisms provides a redundancy of occlusion modalities which greatly increases the success rate of vessel occlusion.

FIG. 16 illustrates an RF energy probe 200 including an RF energy tip 202 and a conducting rod 204. Conducting rod 204 is in electrical communication with an RF energy generator (not illustrated) proximal of handle 38, 138. In a manner which will be readily appreciated by one of ordinary skill in the art, probe 200 can be advanced out distal end 53, 153 of tissue penetrating member 52, 152 to a point adjacent a uterine artery. RF energy is then allowed to flow through conducting rod 204 to tip 202, to heat the uterine artery, adjacent tissues, and blood in the uterine artery to cause the uterine artery to be occluded. According to yet another embodiment, probe 200 can used instead of tissue penetrating member 52, 152, and operated at different power levels: a high power level to advance through the uterine wall; and a lower energy lever to heat the uterine artery, blood in the uterine artery, or both to cause occlusion.

FIG. 17 illustrates a microwave probe 206 including a microwave antenna 208 housed within a protecting sleeve 210. In a manner similar to probe 200, probe 206 can be advanced to a point adjacent a uterine artery of interest, and microwave energy can be emitted from antenna 208 to heat the uterine artery, adjacent tissues, and blood in the uterine artery to cause the uterine artery to be occluded.

Figures 17B, 17C, 17D:
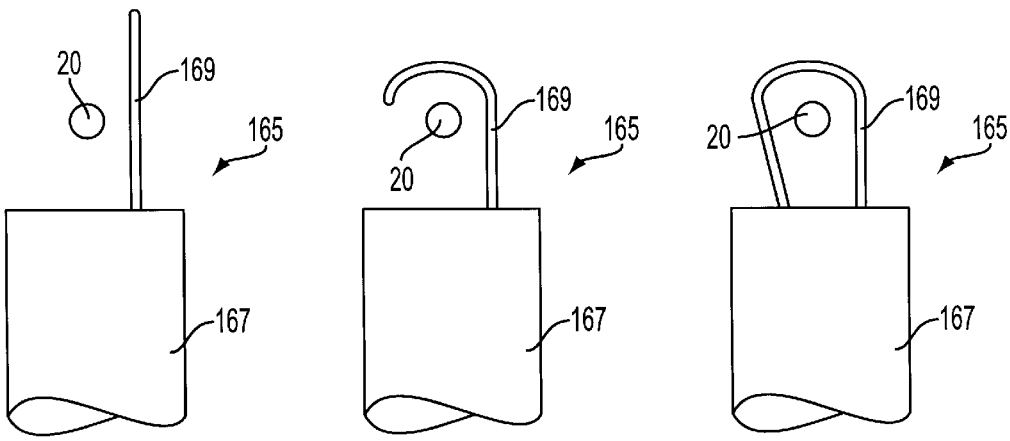

FIGS. 17*a*–17*c* illustrate a probe 165 which includes a tubular member 167 and a wire 169. Wire 169 is movable longitudinally relative to probe 165 to advance the wire distally of the distal end of the probe. Wire 169 is formed of a material which has "memory," i.e., will change shape from a first shape to a second shape when a particular stimulus affects the wire. Preferably, wire 169 is formed of a shape memory alloy (SMA) which has been formed to have a first, straight shape, illustrated in FIG. 17*a*, and a second, curved shaped, illustrated in FIG. 17*c*. More preferably, wire 169 is formed of a shape memory alloy having a transition temperature between about 65° F. (18.3° C.) and about 100° F.(37.8° C.), so that the wire has an open configuration below the transition temperature and a closed configuration above the transition temperature. The details of SMAs and their uses will be understood by one of ordinary skill in the art.

In order to use probe 165 to occlude a uterine artery 20 of interest, probe 165 is maintained at a temperature below its transition temperature, and therefor wire 169 remains in its first, straight shape. It is then advanced through tissue penetrating member 52, 152 to a point adjacent to a uterine artery in a manner so that its temperature remains below the SMAs transition temperature. Wire 169 then heats up because of its intimate contact with tissue, and continues to heat up to reach a steady state temperature near that of the tissue in which it is inserted. As wire 169 heats up to a temperature above the transition temperature of the SMA of which it is formed, the wire begins to change shape toward its second, curved shape, illustrated in FIG. 17b. As wire 169 changes shape as it heats up, the wire loops around uterine artery 20. As wire 169 reaches a temperature close to the temperature of the tissue in which it has been inserted, the wire has completed the transition to its second, curved shape and has snared uterine artery 20 (see FIG. 17c). At this point, wire 169 can be pulled back to crush the uterine artery, and immediately adjacent tissues if necessary or convenient, thus forming an occlusion. Thereafter, wire 169 can be detached from probe 167 and left around uterine artery 20. Alternatively, wire 169 can be cooled by injection of cold fluid, e.g. saline, down tubular member 167 to cause the wire to straighten, because the wire's temperature is dropped below the SMA transition temperature, as will be readily appreciated by one of ordinary skill in the art. When wire 169 is straight, it can then be withdrawn.

Figures 18B, 18C:
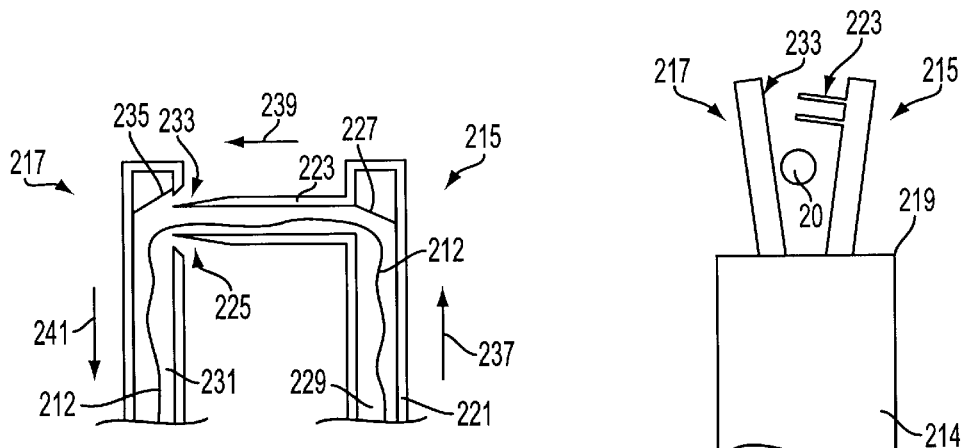
Figure 18A:
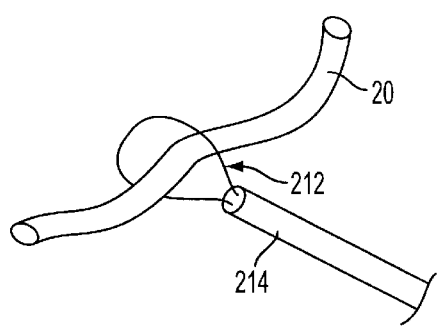
Figure 19:
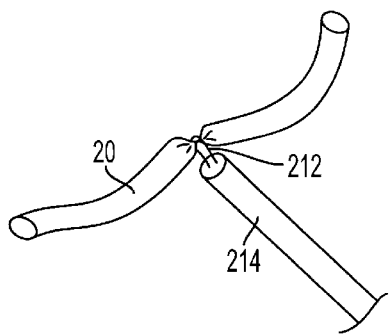

FIGS. 18–19 illustrate a probe 214 which can be used to position a loop or suture 212 around a uterine artery 20 and cinched closed to crush the uterine artery (FIG. 19). Probe 214 includes two tubular members 215, 217 which are movable both proximally and distally relative to a tube 219, but also can pivot toward and away from each other in a manner which will be readily apparent to one of ordinary skill in the art. Tubular member 215 includes a first guide tube 221 and a second guide tube 223 connected to first guide tube 221 at an angle. Second guide tube 223 extends toward and is open toward tubular member 217, and preferably includes a sharpened end 225. First guide tube 221 preferably includes a barrier 227 inside lumen 229, to guide suture 212 into second guide tube 223. Tubular member 217 includes a lumen 231 which opens at a port 233. Preferably, tubular member 217 includes a barrier 235 to guide suture 212 proximally down lumen 231.

To use probe 214 to occlude a uterine artery, the probe is advanced out of a tissue penetrating member 52, 152 so that tubular members 215, 217 are positioned on opposite sides of a uterine artery 20 of interest (see FIG. 18b). Suture material 212 is loaded into lumen 229, preferably by advancing the suture material distally, as indicated by arrow 237. Tubular member 215, 217 are then pivoted toward each other to that sharpened end 225 of second guide tube 223 moves through tissue around uterine artery 20 and seats itself in port 233 of tubular member 217 (see FIG. 18a). A length of suture material 212 is then pushed out of second guide tube 223 in the direction indicated by arrow 239, through port 233, and into lumen 231. Barrier 235 guides suture 212 proximally along lumen 231, in the direction indicated by arrow 241. Then, tubular members 215, 217 are pivoted away from each other and withdrawn into tube 219, leaving a loop of suture material around uterine artery 20 (see FIG. 18). Loop 212 can be either left around uterine artery 20, or released after a predetermined length of time sufficient to ensure that the uterine artery is occluded. If loop 212 is left in place, cinched around artery 20 (see FIG. 19), loop 212 may optionally be formed of a resorbable material which slowly dissolves over time.

Figure 20:
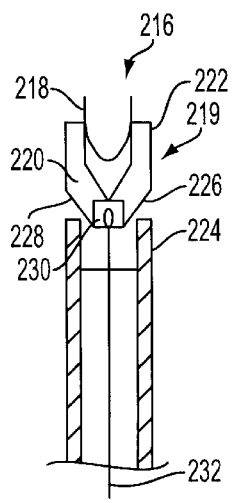
Figure 21:
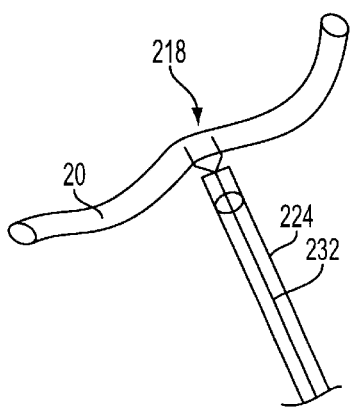
Figure 22:
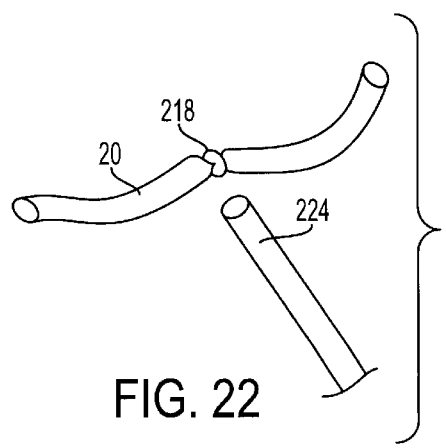

FIGS. 20–22 illustrate a clip applier assembly 216 which includes a clip 218 of a nonresilient, deformable material, and a clamp 219 which both holds the clip and selectively crushes the clip around a uterine artery. Clamp 219 includes a pair of opposed jaws 220, 222, which hold clip 218 between them. Jaws 220, 222 are hinged at a hinge 230. Jaws 220, 222 include bearing surfaces 226, 228, which bear against the distal end of a tube 224 which carries clamp 219 and clip 218. A pullwire 232 extends proximally from hinge 230 to handle 38, 138, and is accessible to the practitioner.

In operation, illustrated in FIGS. 21 and 22, clip applier assembly 216 is advanced through tissue penetrating member 52, 152 to a uterine artery 20 of interest. Clip 218 is advanced around uterine artery 20 (see FIG. 21). Pullwire 232 is then pulled proximally, which pulls clamp 219 partially into tube 224. Bearing surfaces 226, 228 bear against the distal end of tube 224, causing jaws 220, 222 to close and crush both clip 218 and uterine artery 20 therein. Because clip 218 is formed of a non-resilient material, the clip can be left in place around uterine artery 20 (see FIG. 22) either partially or completely occluding the uterine artery.

Figure 23:
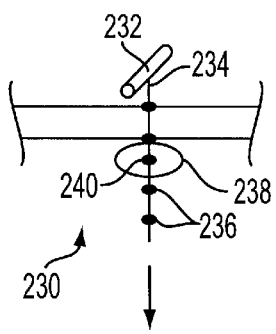
Figure 24:
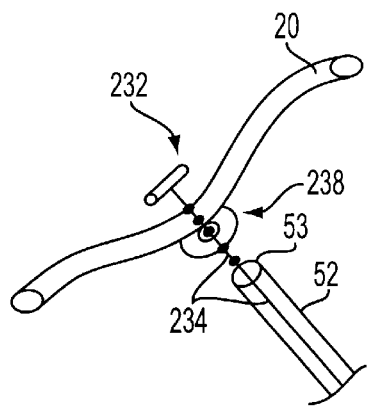
Figure 25:
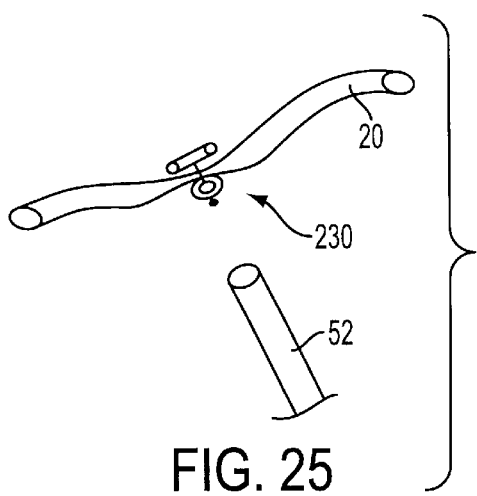

FIGS. 23–25 illustrate a T-bar assembly 230 in accordance with the present invention. T-bar 230 includes an end member 232 having two ends, and an adjustment member 234 attached to the end member between the two ends. Adjustment member 234 includes at least one, and preferably several (five being illustrated in FIGS. 23–25), locking enlargements 236. T-bar assembly 230 also includes a backup disk 238 having a hole 240 therein. As illustrated in FIGS. 23–25, adjustment member 234 extends through backup disk hole 240.

Backup disk 238 is preferably formed of an elastic material having an elastic limit, and backup disk hole 240 is sufficiently smaller than locking enlargement 236, so that the locking enlargement(s) can be pulled through the backup disk hole without exceeding the elastic limit of said elastic material. Thus, adjustment member 234, and therefore the end member 232, can be pulled closer to backup disk 238 and held in this orientation.

According to another embodiment of the present invention, locking enlargement 236 has an asymmetrical shape and backup disk hole 240 is substantially the same shape as the locking enlargement. Backup disk 238 and adjustment member 234 are rotatable relative to each other, so that when the locking enlargement is pulled through the backup disk hole, the locking enlargement and the backup disk hole can be rotated relative to each other so that the locking enlargement asymmetrical shape does not line up with the backup disk hole. Thus, the adjustment member, and therefore the end member 232, are pulled and held closer to the back up disk.

Turning now to FIGS. 24 and 25, T-bar assembly has been advanced to a position adjacent to uterine artery 20 through tissue penetrating member 52, with end member 232 distal of the artery. A proximal end of adjustment member 234 is pulled proximally, while distal end 53 of the tissue penetrating member pushes distally on backup disk 238. The result of these counteracting forces on T-bar assembly 230 is to pinch uterine artery 20 between end member 232 and backup disk 238 as locking enlargements 236 pass through hole 240, and lock the backup disk and end member on either side of the artery. Partial or complete occlusion of uterine artery 20 can be selectively achieved by monitoring blood flow through the artery on an appropriate locating device, e.g., Duplex Doppler ultrasound device, as adjustment member 234 is pulled proximally.

Figure 26:
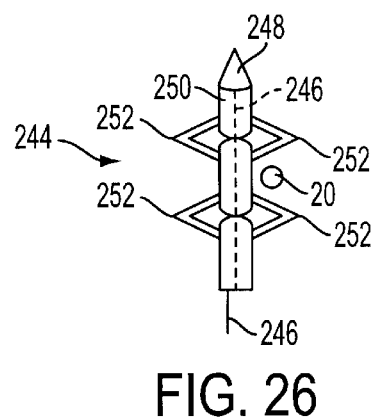
Figure 27:
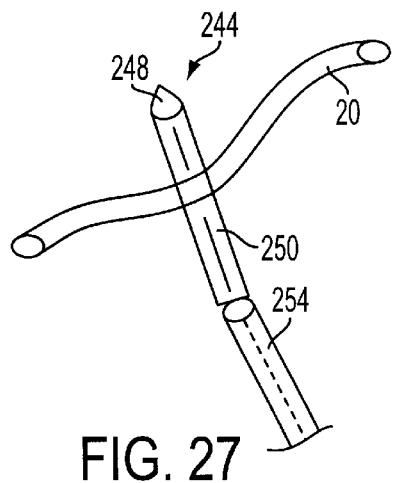
Figure 28:
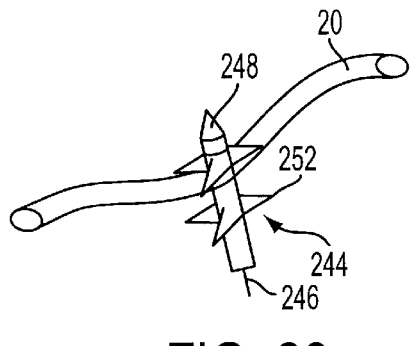

FIGS. 26–28 illustrate a malecot 244 which can be used to occlude a uterine artery 20 in accordance with the present invention. Malecot 244 includes an inner member having a tip 248, and an outer member 250 surrounding the inner member. Outer member 250 and inner member 246 are movable relative to each other, because the outer member includes at least two wings 252 which collapse under pressure. When wings 252 collapse, the wings bend away from inner member 246. Thus, when inner member 246 moves proximally relative to outer member 250, wings 252 bend away from the inner member and toward each other. As illustrated in FIGS. 26 and 28, by positioning uterine artery 20 between wings 252, the uterine artery can be partially or completely occluded.

To occlude a uterine artery 20 with malecot 244, the malecot is advanced through tissue penetrating member 52, 152 (not illustrated in FIGS. 26–28) with a tube 254 to a position adjacent the uterine artery. A proximal end (not illustrated) of inner member 246 is pulled proximally, while tube 254 keeps outer member 250 adjacent to uterine artery 20. The counteracting forces on outer member 250 transmitted by tip 248 and tube 254 cause wings 252 to collapse outward, crushing the uterine artery between them (see FIG. 28). As illustrated in FIG. 28, wings 252 can include several radially separated wings, and at least two sets of wings which are axially separated. Malecot 244 can be left in place, crushing uterine artery 20, by providing a locking mechanism between inner member 246 and outer member 250 (for example, a mechanism like that described with reference to FIGS. 23–25), or can be removed after a predetermined period of time.

FIGS. 29 and 30 illustrate yet another exemplary embodiment of a device which causes occlusion of a uterine artery in accordance with the present invention. As illustrated in FIG. 29, an ultrasonic energy source 256 includes an ultrasonic focusing element 258 which focuses ultrasonic energy at a point 260 in uterine artery 20, and preferably in the sensing plane of the locating device 70 (not illustrated in FIG. 29). The ultrasonic energy thus focused causes high, localized heating within uterine artery 20, which initiates a clotting sequence in the blood therein to form a clot 262. The embodiment illustrated in FIGS. 29 and 30 can be advanced by tissue penetrating member 52, 152 to a position close to uterine artery 20, or alternatively can be housed in cannula 36 with locating device 70, and focused on the uterine artery to initiate blood clotting. Preferably, 256 ultrasonic energy source is capable of emitting ultrasonic energy at a frequency and magnitude sufficient to initiate clotting of human blood by a mechanism including, but not limited, generating cavitation bubbles in human blood, heating human blood, rupturing blood cells, and combinations thereof.

FIG. 31 illustrates yet another exemplary embodiment of a device which causes occlusion of a uterine artery in accordance with the present invention. A mechanical ultrasonic energy source 264 includes an anvil 266 which can be extended distally from tissue penetration member 52, 152. An ultrasonic frequency vibrational energy generator 268 generates ultrasonic energy, and transmits the energy to anvil 266 through a transmission member 270 which extends between the anvil and the ultrasonic frequency vibrational energy generator. Preferably, ultrasonic frequency generator 268 is capable of generating vibrational energy sufficient to initiate a clotting sequence in uterine artery 20 when anvil 266 vibrates. More preferably, ultrasonic frequency generator 268 is capable of generating vibrational energy at a frequency between about 20 kHz and about 50 kHz at a magnitude up to about 0.001 inches ($2.54 \times 10^{-3}$ cm).

Anvil 266 is preferably advanced through tissue penetrating member 52, 152 to a point adjacent uterine artery 20. Ultrasonic frequency vibrational energy generator 268 generates ultrasonic energy, which is transmitted through member 270 to anvil 266, which vibrates and emits vibrational energy. The pressure waves created by the vibrating anvil 266 locally heats uterine artery 20, the blood therein, and the adjacent tissue to a level sufficient to initiate a clotting sequence in the blood, and to disrupt cells in the artery wall. Thus, uterine artery 20 is caused to occlude.

FIG. 32 illustrates yet another exemplary embodiment of a device which causes occlusion of a uterine artery in accordance with the present invention. A probe 272 includes a cannula 274 having a distal end 276 and two lumens 278, 280 which are fluidly isolated from each other along the length of the cannula. The inner lumen 278 preferably conducts a heat transfer fluid distally from proximal portions of the cannula, and outer lumen 280 preferably conducts the heat transfer fluid proximally from the distal tip 282. In distal tip 282, lumens 278, 280 both open into a space 284. Preferably, space 284 provides the only fluid communication between lumens 278, 280. The heat transfer fluid can be either a liquid or a gas, and is at a temperature significantly different from the temperature of a uterine artery of interest. The heat transfer fluid can be either hot, to transfer heat to the uterine artery and adjacent tissues to heat the uterine artery, blood therein, and adjacent tissues. Alternatively, the heat transfer fluid can be cold, e.g., cryogenic, to transfer heat from the uterine artery and adjacent tissues.

To occlude a uterine artery with probe 272, a source of heat transfer fluid (not illustrated) capable of delivering a heat transfer fluid, e.g., hot saline for heating, or liquid nitrogen, liquid oxygen, or other liquified gas for cooling, is placed in fluid communication with inner lumen 278. Probe 272 is advanced distally through tissue penetrating member 52, 152 to a point adjacent a uterine artery of interest, and heat transfer fluid is pumped distally down inner lumen 278. The heat transfer fluid flows to tip 282, reverses direction in space 284, and is drawn proximally up outer lumen 280. Preferably, outer lumen 280 and inner lumen 278 are coaxial. Distal tip 282 becomes and remains at a temperature very different from that of the surrounding tissue, due to the presence of heat transfer fluid in space 284, which induces heat transfer with the uterine artery and adjacent tissues. This heat transfer quickly effects these tissues by heating or cooling the tissues, including the uterine artery, causing the artery wall's cells to die, which initiates a clotting sequence ending in occlusion of the uterine artery.

FIG. 33 illustrates yet another exemplary embodiment of a device which causes occlusion of a uterine artery in accordance with the present invention. An electric heating ablation probe 286 includes a shaft 288, which can be either solid or tubular and hollow, a resistive heating element tip 290 at a distal end of the shaft, and an electrical power transmission wire 292 extending proximally from the resistive heating element tip. As will be readily appreciated by one of ordinary skill in the art, in order to occlude a uterine artery using probe 286, the probe is advanced distally through tissue penetrating member 52, 152 to a point adjacent a uterine artery of interest. Current is allowed to flow through wire 292 to tip 290, which heats up. The heat transfer from tip 290 to the uterine artery, blood therein, and adjacent tissues initiates a clotting sequence ending in occlusion of the uterine artery.

Processes of occluding a uterine artery in accordance with the present invention will now be described with reference to FIGS. 34–45. As will be readily appreciated by one of ordinary skill in the art, the foregoing discussion of particular embodiments of devices in accordance with the present invention is intended to merely provide examples of apparatus and systems that are within the spirit and scope of the present invention. Furthermore, specific features of these several embodiments will not be discussed in the following description of methods of occluding a uterine artery, in order to emphasize these methods. Familiarity with specific features, in particular locating device 70, imaging plane 68, and tissue penetrating member 52, 152 are presumed in the following description.

Figure 34:
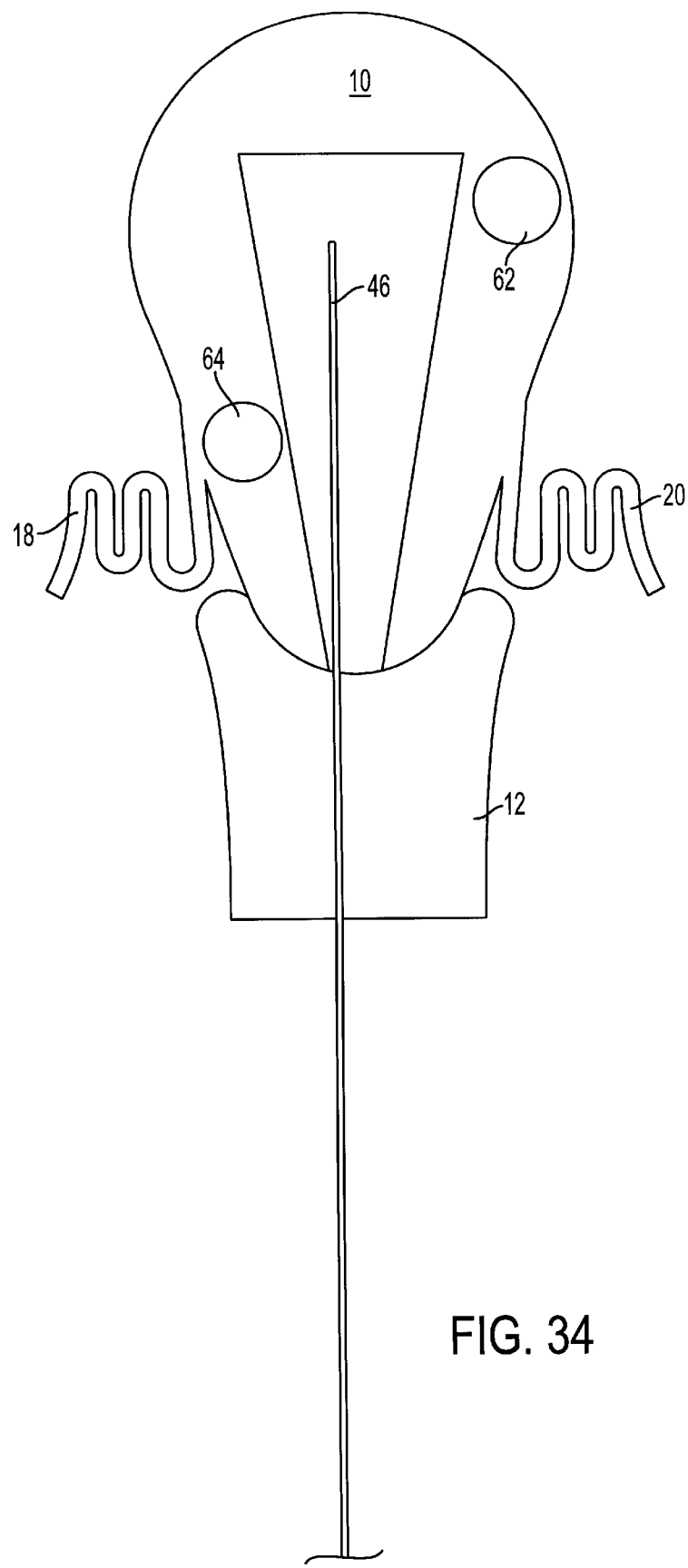
FIGS. 34–39 illustrate an exemplary method of occluding a uterine artery in accordance with the present invention.
Figure 35:
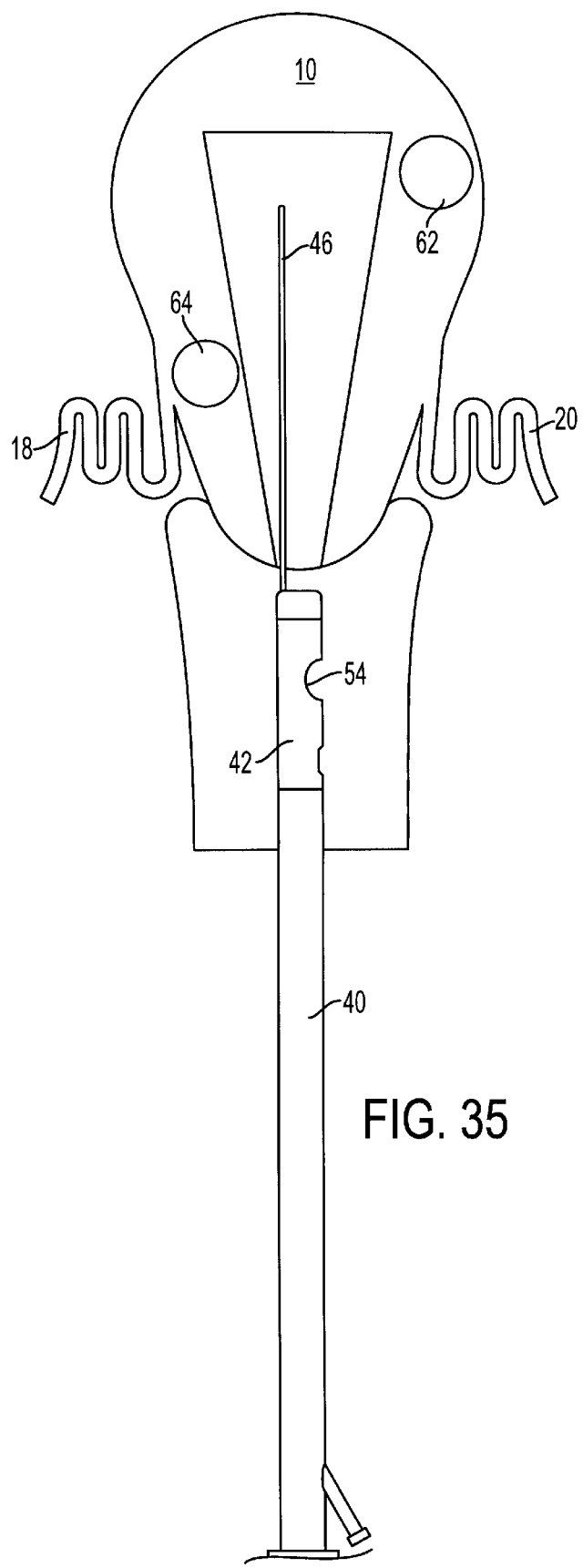
Figure 36:
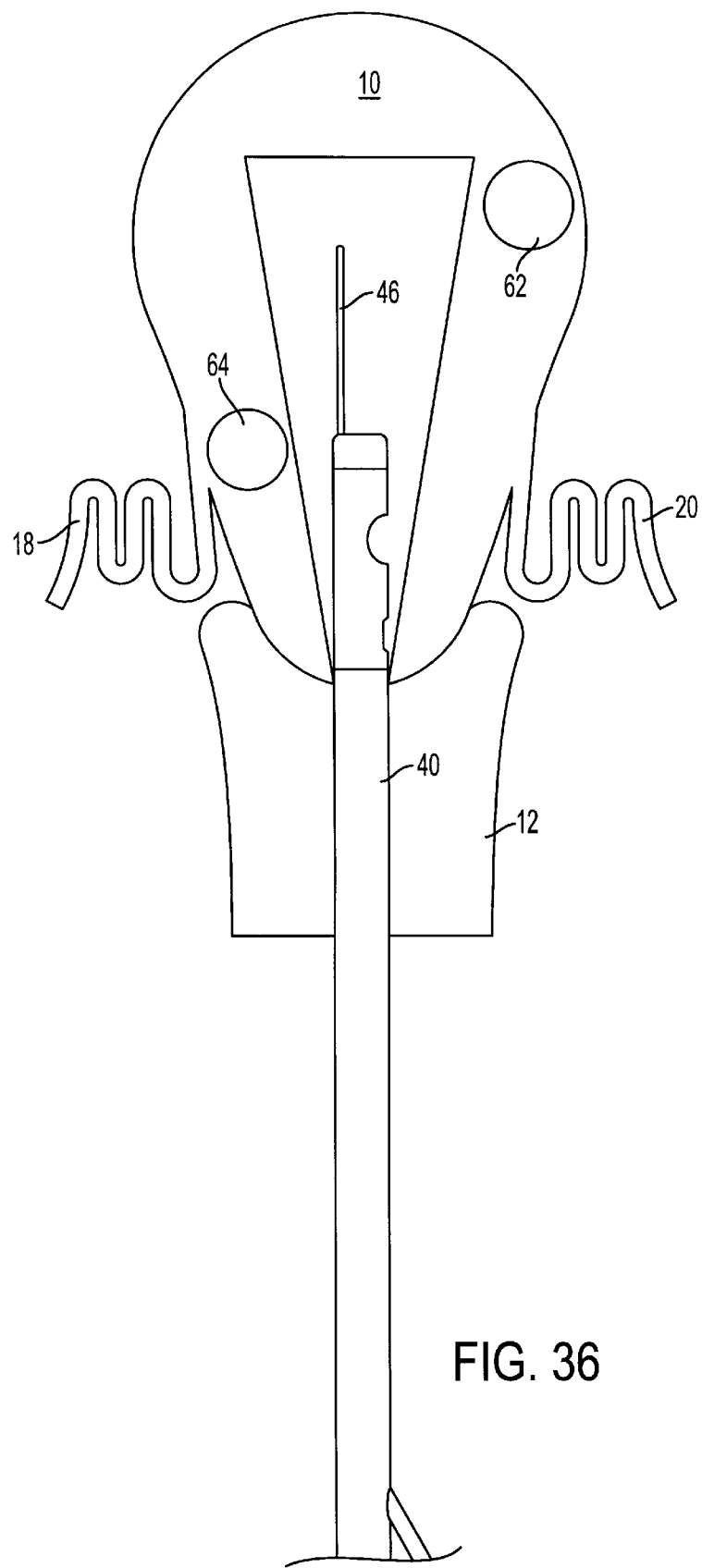

As illustrated in FIG. 34, a patient's uterus 10 is afflicted with two representative fibroids or myomas 62 and 64, which are to be treated using the inventive procedures. Initially, guidewire 46 is extended distally from distal portion 42 of instrument 30 into uterus 10. Then, as illustrated in FIG. 35, cannula 36 is advanced through vagina 12 along guidewire 46, until it is placed within the uterus 10 (FIG. 36).

It should be noted at this point that guidewire 46, although preferred, may optionally not be used, if desired. Alternatively, for example, an integrated dilator at the instrument tip may be employed, which would reduce the required procedural steps.

Figure 37:
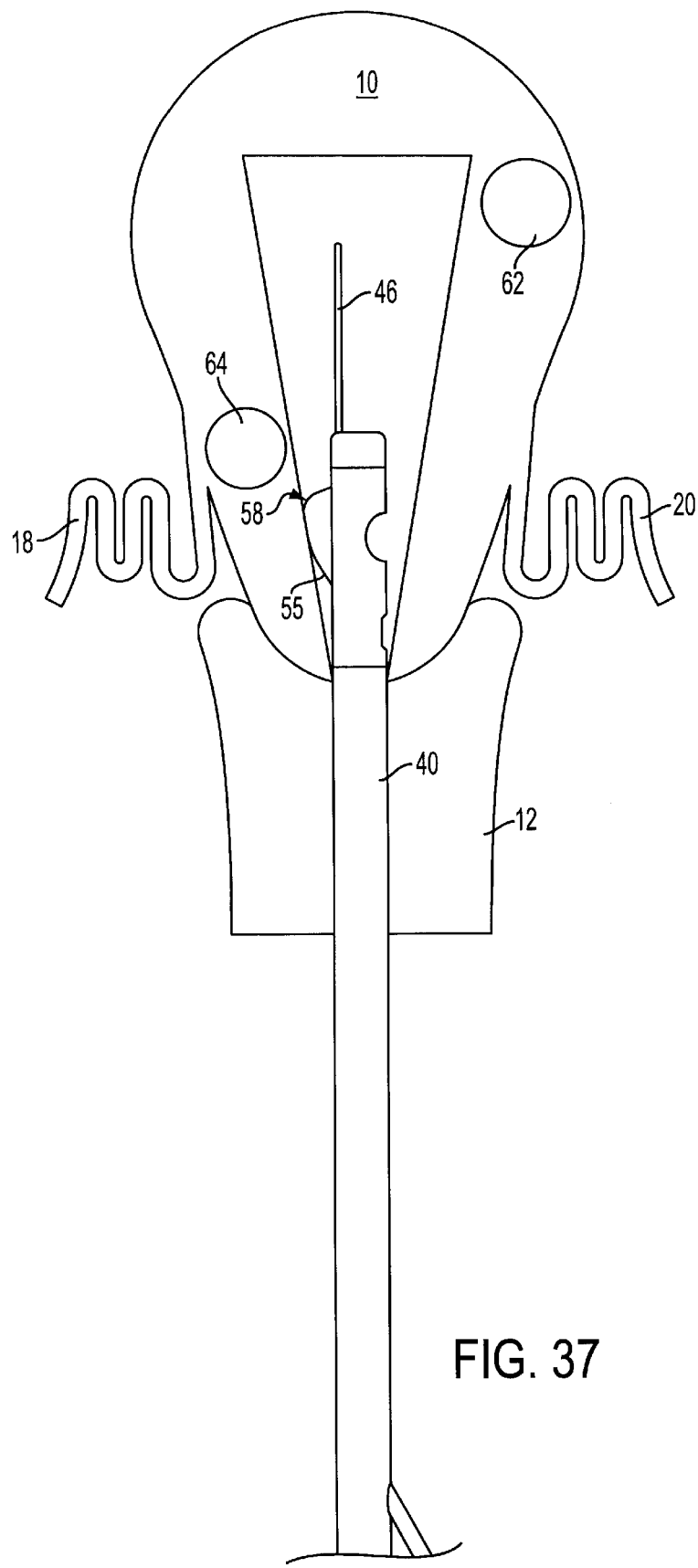
Figure 38:
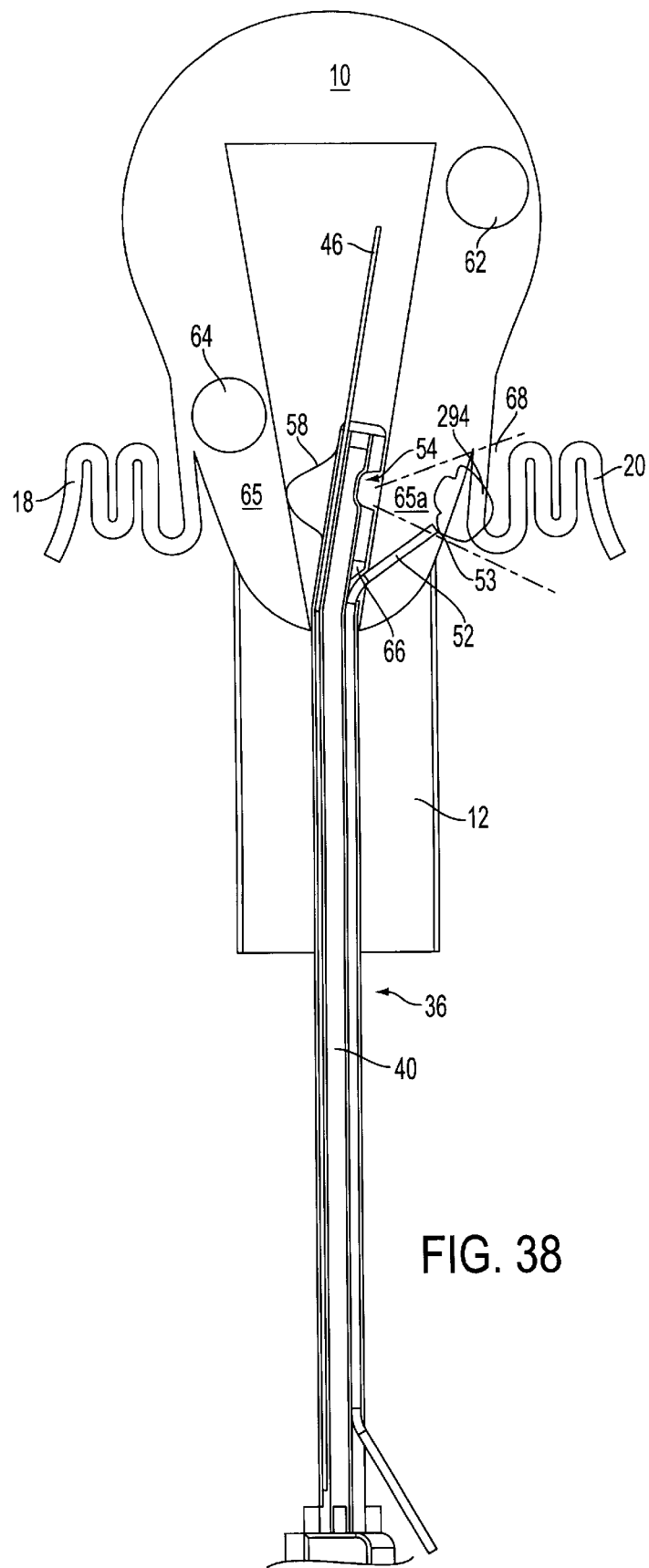

Once cannula 36 is in place within uterus 10, the practitioner is ready to initiate the occluding process with respect to left uterine artery 20. First, as illustrated in FIG. 37, the supporting and deflection element 58, preferably a belt 55 as illustrated, is actuated to extend radially outwardly in the direction shown, so that, as shown in FIG. 38, belt 55 bears against rigid wall 65 of uterus 10, thereby pushing the cannula in the opposing direction. This action ensures that viewing window 54 is disposed against uterine wall 65a adjacent to the uterine artery to be occluded (in this example the left uterine artery 20). This has the further advantage of aiding imaging qualities, because when viewing window 54 actually contacts the uterine wall, the ultrasound gel contact clears the image conveyed to the practitioner and stability of the image is thereby improved. In this regard, it should be noted that in preferable embodiments the portions of shaft 40 proximal and distal of flexible portion 41 are rigid, so that distal portion 42 is moved responsive to extension of supporting and deflection element 58.

Following radial extension of deflection belt 58, tissue penetrating member 52 is advanced toward artery 20, by the practitioner pushing distally on proximal portions of the member. To assist tissue penetrating member 52 in extending laterally relative to the axis 56 and directly into and along imaging or sensing plane 68, a guide ramp 66 is preferably provided (see FIG. 38) for the distal end of tissue penetrating member 52 to push against as it is displaced distally. During the distal advancement of tissue penetrating member 52 into uterine wall 65a, RF energy may be supplied to the tissue penetrating member to simultaneously cut a channel into which to advance the member, and cauterize the channel.

Figure 39:
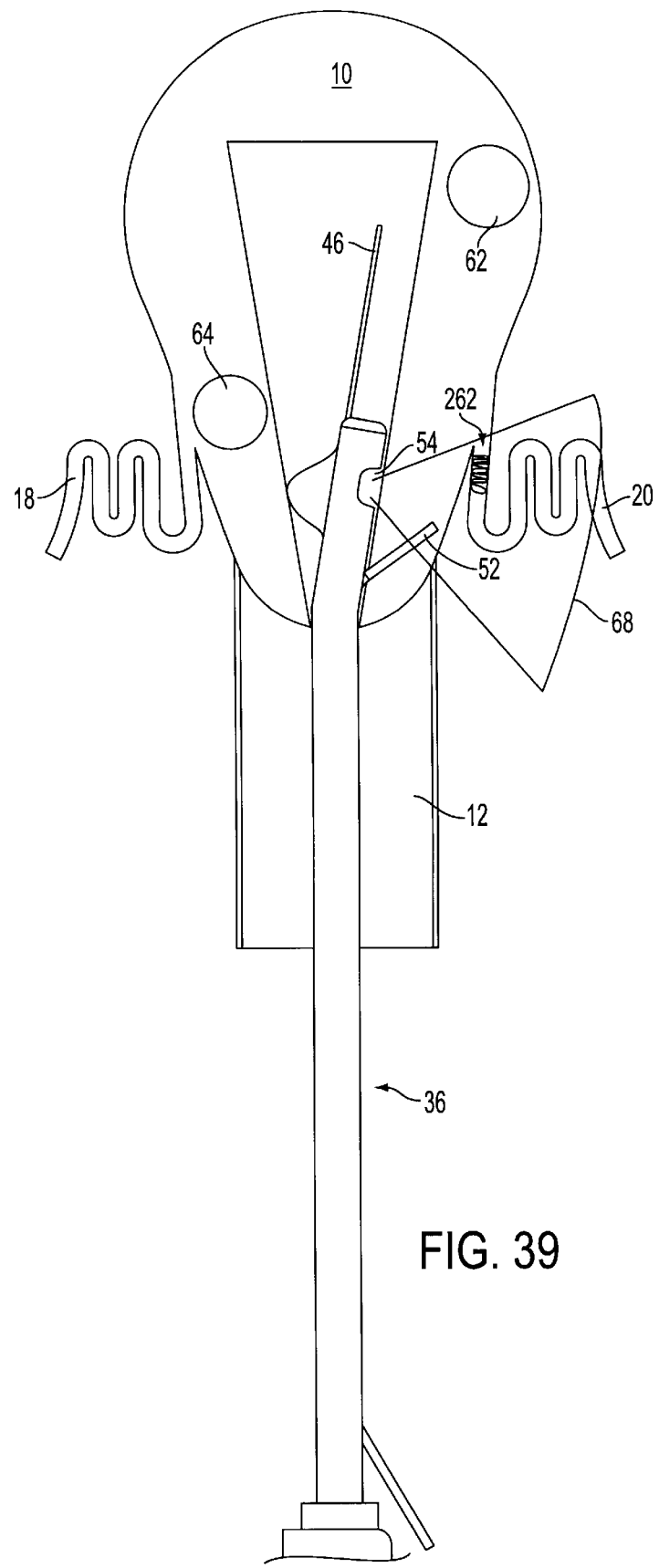

FIG. 39 illustrates cannula 36 when tissue penetrating member 52 is disposed with distal end 53 adjacent to uterine artery 20. In the embodiment illustrated in FIG. 39, a chemical occluding agent, e.g., EtOH 294, has been injected along lumen 59 (see FIG. 6) of the tissue penetrating member and into the tissues surrounding the artery. Preferably, lumen 59 is constructed of or coated with a material which is non-reactive to the chemical occluding agent. As described in greater detail above, the chemical occluding agent, e.g. EtOH, will kill the tissues with which it makes contact, including left uterine artery 20, and thus initiates a clotting sequence which results in occlusion of the uterine artery. As illustrated in FIG. 39, an imaging (preferably ultrasonic) plane 68 is transmitted through viewing window 54 to guide the practitioner as tissue penetrating member 52 is maneuvered radially outwardly to approach uterine artery 20 to be occluded. An occlusion 262 forms in the artery as a result.

After artery 20 is occluded, as illustrated in FIG. 39, cannula 36 may be withdrawn from the uterus along guidewire 46. Then, if artery 18 has not yet been occluded, the practitioner will preferably repeat the procedural steps outlined supra with cannula 36 oppositely oriented in order to occlude artery 18.

Instead of injecting EtOH 294, any of the mechanisms of occlusion within the scope of the present invention can be employed to occlude the uterine artery. As described in greater detail above, all of the modalities and mechanisms in accordance with the present invention are capable of occluding the uterine artery; the foregoing description which made reference to FIGS. 34–39 is merely exemplary, and one of ordinary skill in the art will readily appreciate the processes of employing these mechanisms to occlude a uterine artery.

It is also within the scope of this invention that, alternatively to the employment of an imaging system as described above, a simple landmark/anatomical reference point approach may be employed, wherein cannula 36 may be moved distally a predetermined distance past the cervical os, usually using a set of reference markings (i.e., bands) on the cannula outer surface so that the practitioner knows with certainly the depth to which the instrument has been inserted. Once inserted to the proper position, the instrument is then rotated to a predetermined clock position (i.e., 3 o'clock) to occlude an artery, and to a second predetermined clock position (i.e. 9 o'clock) to occlude a second artery (see FIG. 10).

Rather than using an intrauterine approach to occlude arteries 18 and 20, a transvaginal approach may alternatively be used in accordance with the present invention. This approach may be particularly advantageous if the patient has a uterine configuration which increases the difficulty of employing the intrauterine procedure described above. For example, a retroflex or anteflex uterine configuration might indicate a transvaginal approach. Cannula 136, illustrated in FIG. 12, is suitable for occluding a uterine artery in such a procedure.

Figure 40:
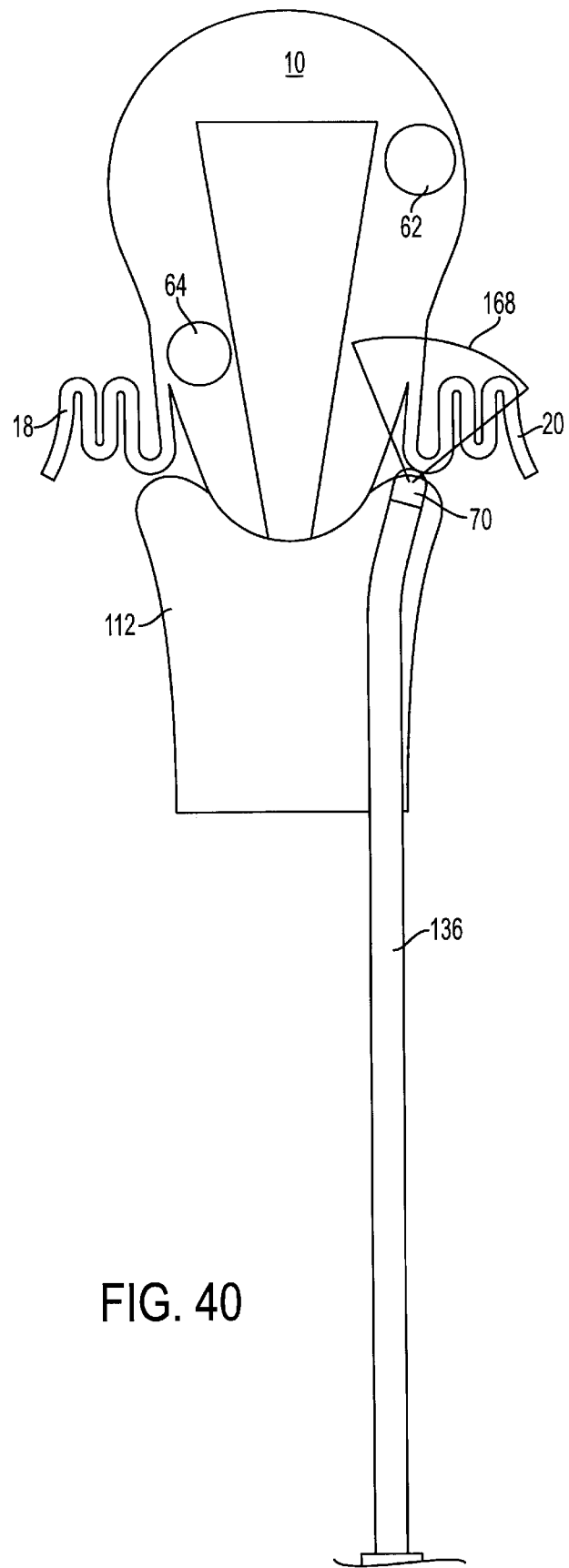
FIGS. 40–42 illustrate a second exemplary method of occluding a uterine artery in accordance with the present invention.
Figure 41:
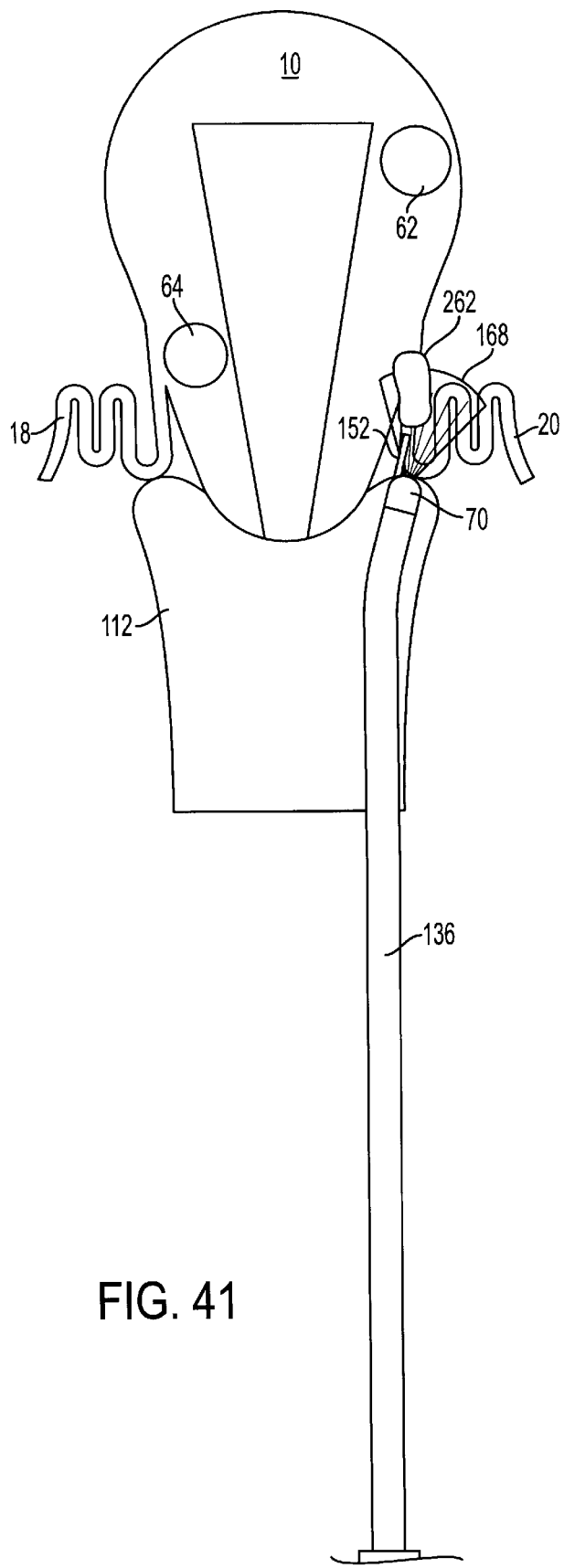
Figure 42:
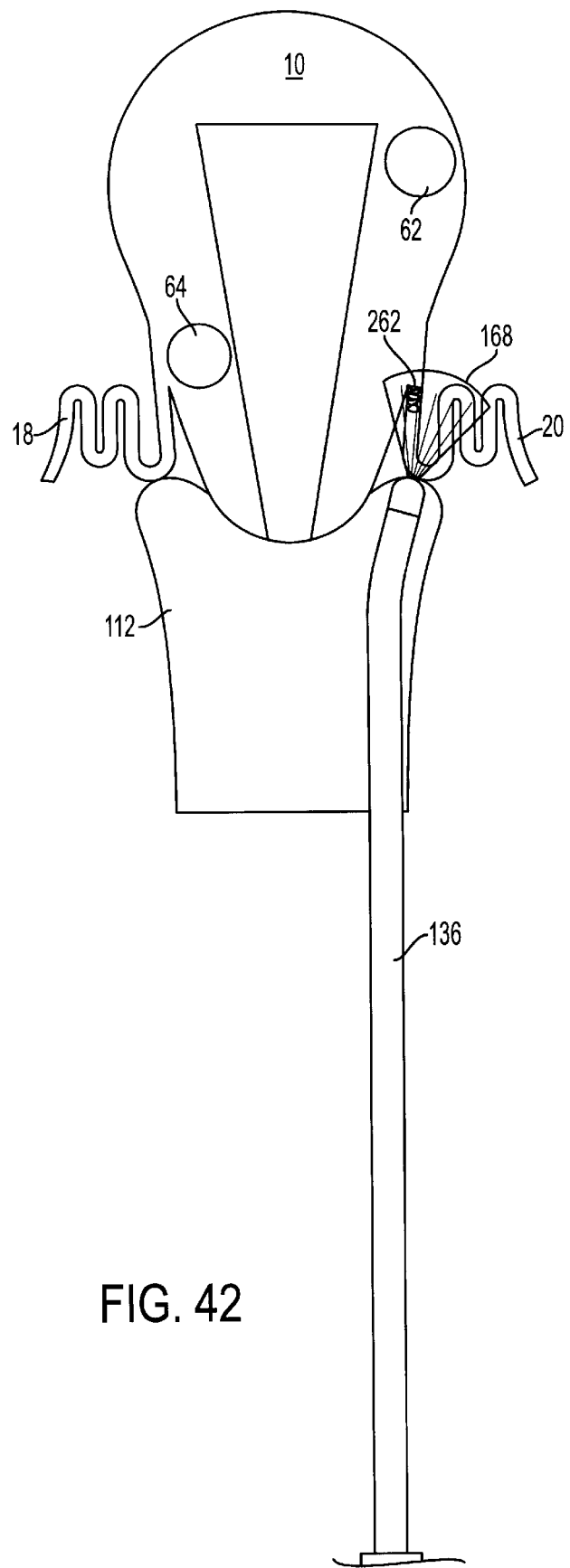

Turning to FIG. 40, cannula 136 is inserted through the vagina 112 until it approaches the artery 20 to be occluded. Then, image plane 168 from locating device 70 is utilized to advance cannula 136 to a position adjacent to artery 20. Once in position, tissue penetrating member 152, which may be any of the embodiments previously described, is activated to occlude the artery (see FIG. 41). Tissue penetrating member 152 is thereafter withdrawn, as illustrated in FIG. 42, leaving an occlusion 262. The procedure may then be repeated to occlude the other artery 18. As discussed supra, bilateral occlusion is important to ensure that the fibroids 62, 64 are fully treated.

Figure 43:
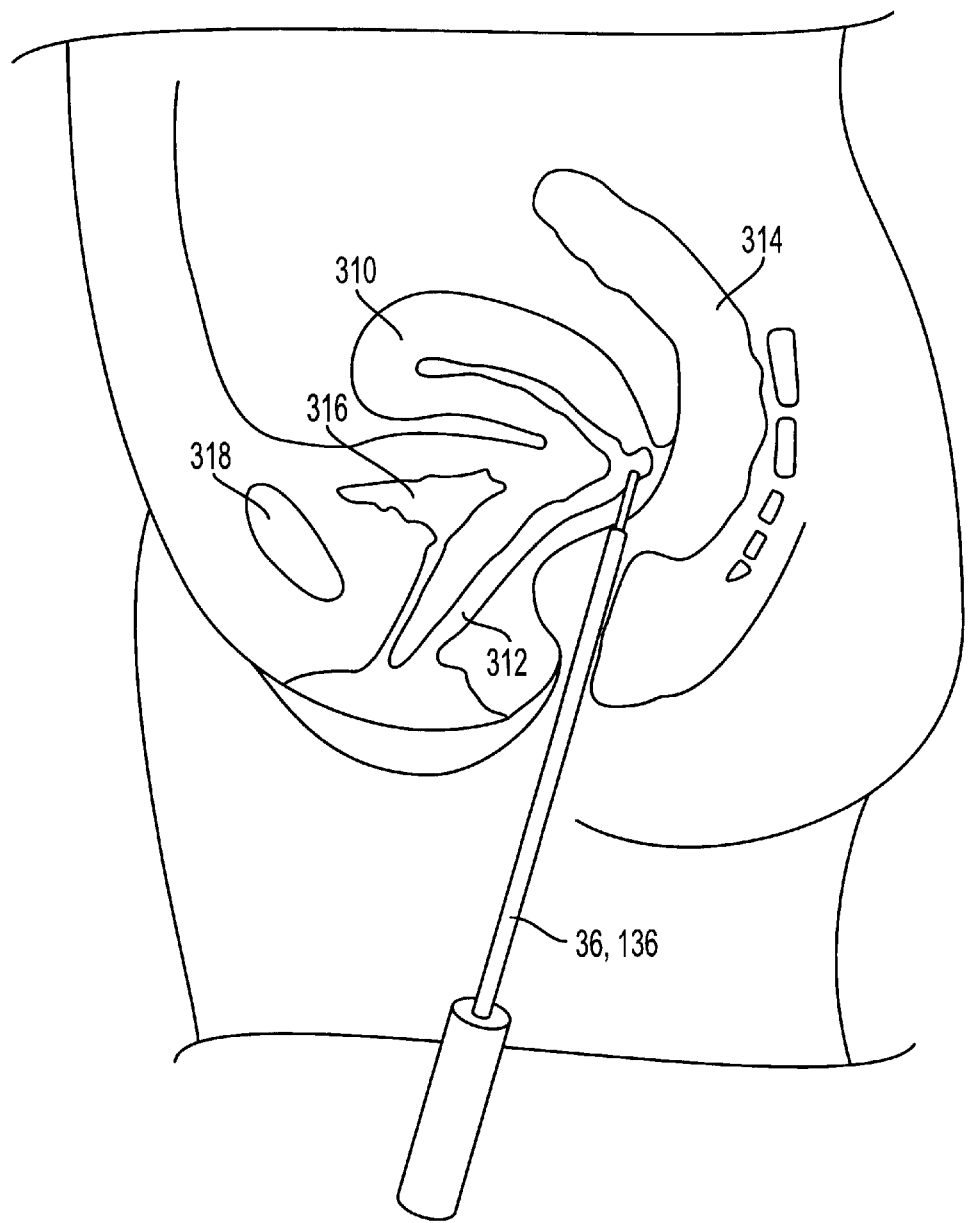
FIG. 43 illustrates yet another exemplary method of occluding a uterine artery in accordance with the present invention, by a transrectal approach.

While the preferred application of the present invention is the bilateral occlusion of the uterine arteries, either transvaginally or trans-uterally, it is within the scope of the invention to employ a trans-rectal or retroperitoneal procedure as well, and/or to utilize apparatus in accordance with the present invention to occlude other arteries or vessels. For example, as illustrated in FIG. 43, there is shown a trans-rectal approach for occluding the uterine arteries. Thus, by way of orientation, FIG. 43 illustrates the uterus 310, vagina 312, rectum 314, urinary bladder 316, and pubic bone 318.

When it is desired to occlude one or more uterine arteries, which extend in and out of the plane of FIG. 43 and are, therefore, not illustrated, cannula 36, 136 is inserted through the rectum using known imaging techniques, until its distal portion 42, 142 (see FIGS. 5 and 12) is disposed adjacent to the uterine artery to be occluded, at which point the occluding tip (not shown) is actuated to occlude the artery, in a manner similar to that disclosed supra with respect to the previous embodiments. Either cannula type (i.e., sideviewing cannula 36 or endviewing cannula 136) may be utilized in this trans-rectal procedure, although the latter instrument, having an "end-view" window 154, may be preferred in most instances.

Figure 44:
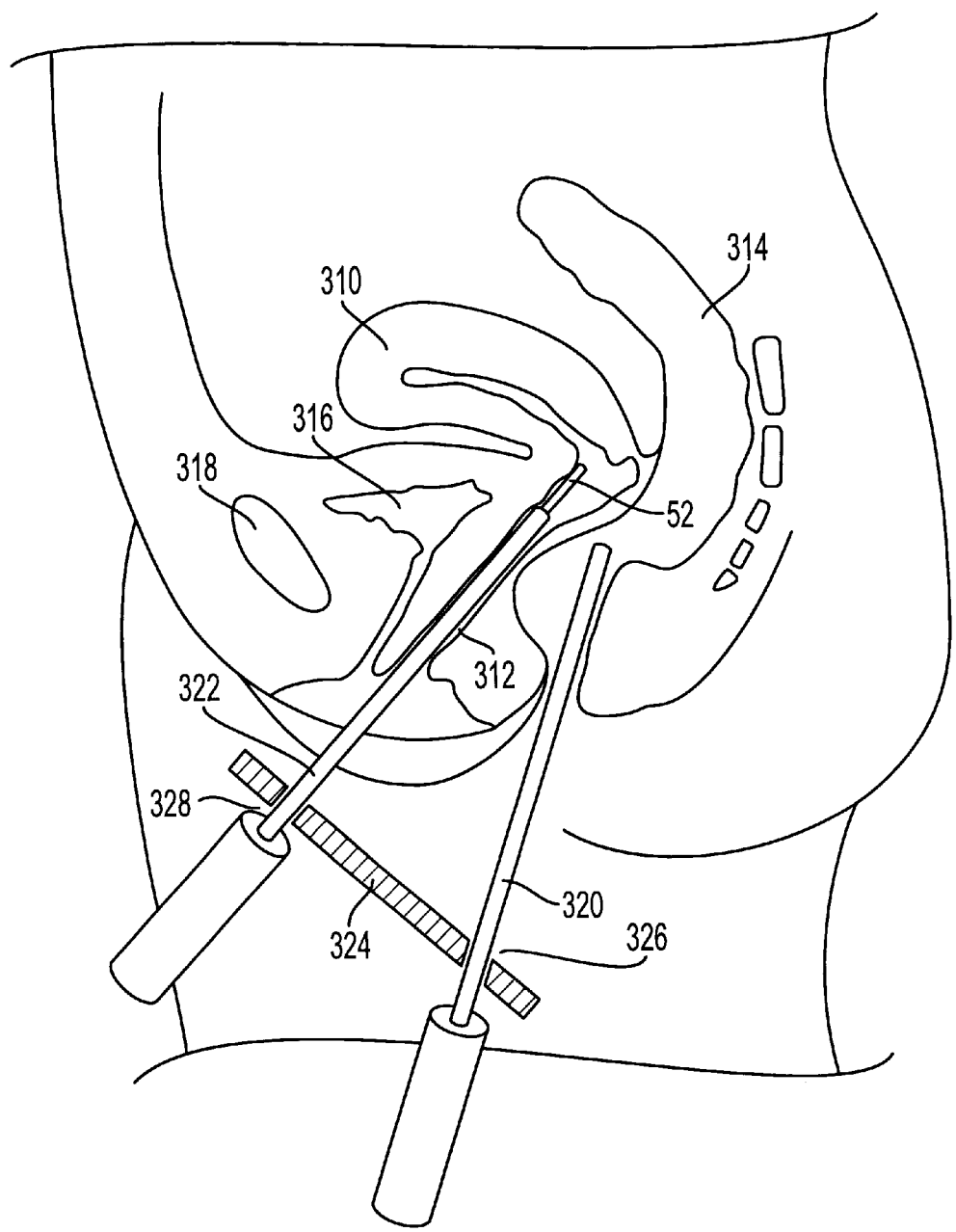
FIG. 44 illustrates yet another exemplary method of occluding a uterine artery in accordance with the present invention, by a combined transrectal and transvaginal approach.

Alternatively, two of the functions of cannulae 36, 136, i.e., locating and occluding, can be separately performed by separate cannulae, as illustrated in FIG. 44. Still utilizing a trans-rectal approach similar to that illustrated in FIG. 43, an imaging cannula 320 is inserted into rectum 314, while cannula 322, which includes a tissue penetrating member 52 extending out a distal end thereof, is inserted into vagina 312 in a manner similar to the method described above with reference to FIG. 40. Cannulae 320, 322 are preferably held together by a template or block 324, which includes holes 326, 328 through which cannulae 320,322 are slidably held. Block 324 is designed so that tissue penetrating member 52 will extending into imaging plane 68 (not illustrated) of cannula 320, in a manner similar to the prior embodiments.

Figure 45:
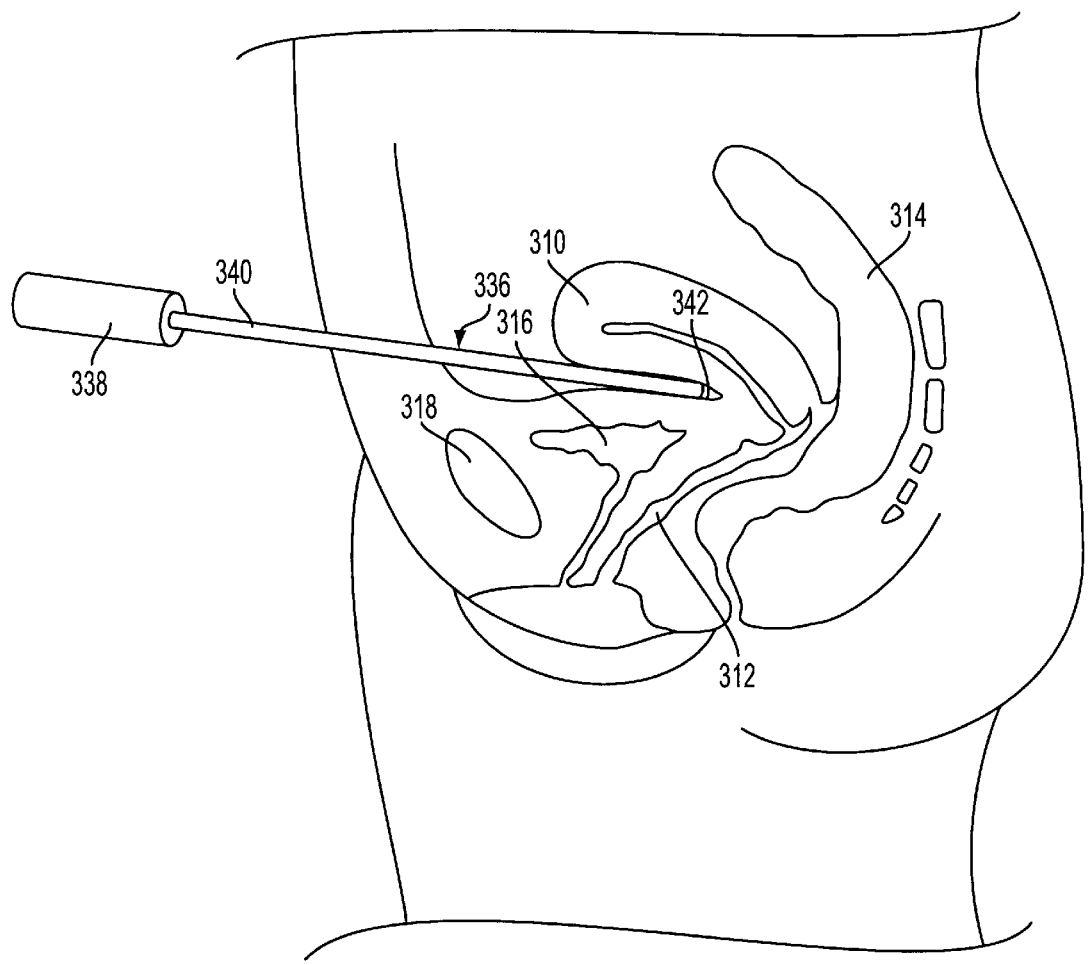
FIG. 45 illustrates yet another exemplary method of occluding a uterine artery in accordance with the present invention, by a retroperitoneal approach.

FIG. 45 illustrates an inventive retroperitoneal approach for occluding the uterine arteries, in accordance with the principles of the present invention. Using a retroperitoneal approach, a standard laparoscopic procedure is initiated, typically employing a trocar (not illustrated) for providing access for cannula 336, moving the bowel and insulating the abdomen. Either an endoscope or an ultrasound imaging system is preferably used to guide advancement of the instrument through the abdomen to the vicinity of the uterine artery to be occluded, at which point a tissue penetrating member (not illustrated) is actuated to occlude the artery, in a manner similar to that disclosed above with respect to the numerous prior embodiments. Either cannula type may be utilized in this retroperitoneal procedure, although the latter instrument, having an "end-view" window 154, may be preferred in most instances.

In accordance with yet another embodiment of the present invention, the locating function performed by the devices described above can be performed by an external device, such as a CT scan (with or without contrast agents), fluoroscopy, radiocontrast angiography, or a MRI device. These locating devices can be used to generate a coordinate system in the patient to which the practitioner correlates the position of an instrument similar to instrument 30. In this embodiment, however, the instrument does not include a locating system in the cannula, but rather includes the structures of cannula 36 for penetrating tissue to gain access to the uterine arteries. By locating the uterine artery of interest with the locating system's cursor, the practitioner can then correlate the position of the cursor with the position of the tissue penetrating member, and thereby carry out the methods described above with the cannula. Because these locating devices provide three dimensional images of anatomical structures, and will also reveal the relative location of the cannula to the uterine arteries, the locating devices can be used to guide the practitioner to the uterine artery of interest with accuracy.

While the invention has been described in detail with reference to preferred embodiments thereof, it will be apparent to one skilled in the art that various changes can be made, and equivalents employed, without departing from the scope of the invention.

What is claimed is:

1. A method of treating a female patient's uterus, comprising:

providing an occluding system having a pressure applying mechanism configured to compress a blood vessel and a blood vessel sensor;

inserting the occluding system into the female patient to access a region adjacent a uterine artery leading to the patient's uterus;

locating the uterine artery with the blood vessel sensor; and occluding the located uterine artery by compressing the located uterine artery with the pressure-applying mechanism of said occluding system to at least partially cut off blood flow through the located uterine artery to the patient's uterus.

2. The method of claim 1, wherein the occluding system penetrates tissue to access a region adjacent a uterine artery.

3. The method of claim 2, wherein the tissue penetrated by the occluding system includes abdominal tissue.

4. The method of claim 1, wherein the occluding system is inserted into a body cavity of the patient.

5. The method of claim 4, wherein said body cavity is a vagina.

6. The method of claim 4, wherein said body cavity is a uterus.

7. The method of claim 4, wherein said body cavity is a rectum.

8. The method of claim 4, wherein said body cavity is a peritoneal cavity.

9. The method of claim 1, wherein the occluding system accesses an anatomical region adjacent to the uterine artery and an ultrasonic transducer senses the location of anatomical structures in a sensing plane.

10. A method of treating a female patient in accordance with claim 1, wherein said female patient has a uterine fibroid.

11. A method of claim 1, wherein the uterine artery is located with a blood vessel sensor selected from the group consisting of a CT scanner, a fluoroscope, X ray, a MRI device, Doppler audio device, a gray scale color 2D Doppler ultrasound device, a landmark system, and combinations thereof.

12. A method of claim 1, wherein the occluding system is inserted into a body cavity along a path selected from the group consisting of a path along a uterine wall, a path along a vaginal wall, a path along a rectal wall, a path through a uterine wall, a path through a vaginal wall, a path through a rectal wall, and a path into a peritoneal cavity.

13. A method of treating a female patient in accordance with claim 1, wherein said occluding said uterine artery comprises temporarily occluding said uterine artery.

14. A method of treating a female patient in accordance with claim 1, wherein occluding said uterine artery comprises permanently occluding said uterine artery.

15. A method of treating a female patient in accordance with claim 1, wherein occluding said uterine artery comprises completely occluding said uterine artery.

16. A method of claim 1, wherein the uterine artery is compressed with a pressure-applying mechanism selected from the group consisting of a pair of opposed jaws, a clip, a T-bar, a loop, a snare, a coil, a spring, a malecot, and a staple.

17. The method of claim 1, wherein the blood vessel sensor comprises a blood vessel locating device selected from the group consisting of an ultrasound imaging device, a Doppler ultrasound device, a landmarking system applied to a device, a computer-aided tomography (CAT) scanner, a fluoroscope, an angiography device, and a magnetic resonance imaging (MRI) device.

18. A method of treating a female patient's uterus, comprising the steps of:

providing an occluding system having a pressure applying mechanism configured to compress a blood vessel and a blood vessel sensor;

inserting the occluding system into the female patient to access a region adjacent a uterine artery leading to the patient's uterus;

locating the uterine artery with the blood vessel sensor; and occluding the located uterine artery by compressing the located uterine artery with the pressure-applying mechanism of said occluding system to at least partially cut off the blood supply through the located uterine artery to the patient's uterus.

19. A method of treating a female patient's uterus, comprising:

providing an occluding system having a pair of opposed pressure applying jaws;

advancing the occluding system within the female patient to a region adjacent a uterine artery leading to the patient's uterus;

locating the uterine artery with a blood vessel sensor; and occluding the located uterine artery by at least partially closing the opposed pressure applying jaws of the occluding system against the located uterine artery to at least partially cut off the blood flow through the located uterine artery to the patient's uterus.

* * * * *